US012642943B2

(12) United States Patent
Vikash et al.

(10) Patent No.: US 12,642,943 B2
(45) Date of Patent: Jun. 2, 2026

(54) CATHETER SYSTEM HAVING A PUSH BUTTON NEEDLE RETRACTION MECHANISM

(71) Applicant: Becton, Dickinson and Company, Franklin Lakes, NJ (US)

(72) Inventors: Deepan Vikash, Tamil Nadu (IN); Sakthivel Karthikeyan, Coimbatore (IN); S. Ray Isaacson, Layton, UT (US); Jonathan Karl Burkholz, Salt Lake City, UT (US); Sridhaar Nandakumar, Tamil Nadu (IN); Prasad Govindaraj, Tamil Nadu (IN)

(73) Assignee: Becton, Dickinson and Company, Franklin Lakes, NJ (US)

( * ) Notice: Subject to any disclaimer, the term of this patent is extended or adjusted under 35 U.S.C. 154(b) by 505 days.

(21) Appl. No.: 18/139,732

(22) Filed: Apr. 26, 2023

(65) Prior Publication Data

US 2023/0390530 A1    Dec. 7, 2023

Related U.S. Application Data

(60) Provisional application No. 63/349,917, filed on Jun. 7, 2022.

(51) Int. Cl.
*A61M 25/06* (2006.01)
*A61M 25/00* (2006.01)

(52) U.S. Cl.
CPC ........ *A61M 25/06* (2013.01); *A61M 25/0097* (2013.01)

(58) Field of Classification Search
CPC .......... A61M 25/0606; A61M 25/0631; A61M 25/0097; A61M 25/06; A61M 2005/3247
See application file for complete search history.

(56) References Cited

U.S. PATENT DOCUMENTS 5,501,675 A * 3/1996 Erskine ............. A61M 25/0631
                                                    604/164.12
2004/0116855 A1 6/2004 Popov
2021/0154437 A1 5/2021 Scherich

FOREIGN PATENT DOCUMENTS

EP          1907042 B1 * 3/2009

* cited by examiner

*Primary Examiner* — Theodore J Stigell
(74) *Attorney, Agent, or Firm* — Kirton McConkie; Whitney Blair; Kevin Stinger

(57) ABSTRACT

A catheter system may include a catheter assembly, which may include a catheter adapter and a catheter. The catheter system may include a needle assembly, a barrel, an introducer needle comprising a sharp distal tip, a needle hub coupled to the introducer needle and movably disposed within the barrel, and a spring disposed within the barrel. The catheter system may include a push button disposed in a locked position such that depression of the push button is inhibited. The push button may be configured to slide laterally or distally from the locked position to an unlocked position. When the push button is in the unlocked position and the barrel is spaced apart from the catheter adapter, the push button may be configured to depress. In response to depression of the push button, the spring may be configured to expand proximally and move the needle hub proximally within the barrel.

9 Claims, 28 Drawing Sheets

34

36

40

52

98          132

134

130

52

98

54

132

134

136

56

CATHETER SYSTEM HAVING A PUSH BUTTON NEEDLE RETRACTION MECHANISM

RELATED APPLICATIONS

This application claims priority to U.S. Patent Application No. 63/349,917, filed Jun. 7, 2022, entitled CATHETER SYSTEM HAVING A PUSH BUTTON NEEDLE RETRACTION MECHANISM, which is incorporated herein in its entirety.

BACKGROUND

A common type of catheter assembly includes a peripheral intravenous catheter ("PIVC") that is over-the-needle. As its name implies, the PIVC that is over-the-needle may be mounted over an introducer needle having a sharp distal tip. The catheter assembly may include a catheter adapter, the PIVC extending distally from the catheter adapter, and the introducer needle extending through the PIVC. The PIVC and the introducer needle may be assembled such that the distal tip of the introducer needle extends beyond the distal tip of the PIVC with the bevel of the needle facing up away from skin of the patient immediately prior to insertion into the skin. The PIVC and the introducer needle are generally inserted at a shallow angle through the skin into vasculature of the patient.

In order to verify proper placement of the introducer needle and/or the PIVC in the blood vessel, a clinician may confirm that there is flashback of blood in a flashback chamber of the catheter assembly. Once placement of the introducer needle has been confirmed, the clinician may remove the introducer needle, leaving the PIVC in place for future blood withdrawal or fluid infusion.

In some instances, the catheter assembly, such as the BD INSYTE™ AUTOGUARD™ Shielded IV Catheter, may include a push button configured to retract the introducer needle after the PIVC is in place within the vein. The push button may be accidentally or inadvertently activated before venipuncture completion, such as, for example, during assembly, packaging, shipping, or removal from packaging.

The subject matter claimed herein is not limited to embodiments that solve any disadvantages or that operate only in environments such as those described above. Rather, this background is only provided to illustrate one example technology area where some implementations described herein may be practiced.

SUMMARY

The present disclosure relates generally to vascular access devices and related methods. More particularly, the present disclosure relates to a catheter system that includes a push button needle retraction mechanism, as well as related devices and methods. In some embodiments, the push button safety device may prevent accidental or inadvertent retraction of an introducer needle before venipuncture is complete.

According to a first set of embodiments, a catheter system may include a catheter assembly, which may include a catheter adapter. The catheter adapter may include a distal end, a proximal end, and a catheter adapter lumen extending through the distal end of the catheter adapter and the proximal end of the catheter adapter. The catheter system may include a catheter extending from the distal end of the catheter adapter. The catheter system may include a needle assembly, which may include one or more of a barrel, an introducer needle having a sharp distal tip, a needle hub coupled to the introducer needle and movably disposed within the barrel, and a spring disposed within the barrel.

The catheter system may include a push button disposed in a locked position such that depression of the push button is inhibited. The push button may be configured to slide laterally from the locked position to an unlocked position. When the push button is in the unlocked position and the barrel is spaced apart from the catheter adapter, the push button may be configured to depress. In response to depression of the push button, the spring may be configured to expand proximally and move the needle hub proximally within the barrel to retract the introducer needle proximally.

An upper surface of the push button may include a tab generally perpendicular to a longitudinal axis of the catheter system. An upper surface of the push button may be sloped upwardly in a direction of lateral sliding of the push button from the locked position to the unlocked position. The upper surface of the push button may facilitate lateral sliding of the push button.

The push button may include a projection, which may extend in a distal direction. A distal end of the projection may include an arm. The arm may extend in an opposite direction as a direction of lateral sliding of the push button from the locked position to the unlocked position. The needle hub may include a slot. When the push button is in the locked position, the arm may be disposed within the slot to inhibit depression of the push button. In response to the push button sliding laterally, the arm may be configured to remove from the slot to move the push button from the locked position to an unlocked position.

An edge of the push button may be spaced apart from an edge of the barrel to a create a gap between the push button and the barrel. In response to the push button sliding laterally from the locked position to an unlocked position, the push button may close the gap. The push button may include an opening. The needle hub may extend through the opening. The opening may include an upper arc proximate a lower arc. A center of a circle formed by the upper arc may be offset from a center of a circle formed by the lower arc. When the push button is in the locked position, the needle hub may be aligned with the center of the circle formed by the lower arc. When the push button is in the unlocked position, the needle hub may be aligned with the center of the circle formed by the upper arc.

A distal face of the push button contacting the barrel may include one or more pads to reduce friction between the push button and the barrel. The push button may include a protrusion contacting an edge of the barrel when the push button is in the locked position. In response to the push button sliding laterally from the locked position to the unlocked position, the protrusion may be moved internal to the edge of the barrel such that the push button is configured to depress when the barrel is spaced apart from the catheter adapter.

According to a second set of embodiments, a catheter system may include a catheter assembly, which may include a catheter adapter. The catheter adapter may include a distal end, a proximal end, and a catheter adapter lumen extending through the distal end of the catheter adapter and the proximal end of the catheter adapter. The catheter system may include a catheter extending from the distal end of the catheter adapter. The catheter system may include a needle assembly, which may include one or more of a barrel, an introducer needle having a sharp distal tip, a needle hub coupled to the introducer needle and movably disposed within the barrel, and a spring disposed within the barrel.

The catheter system may include a push button disposed in a locked position such that depression of the push button is inhibited. The push button may be configured to slide distally from the locked position to an unlocked position. When the push button is in the unlocked position and the barrel is spaced apart from the catheter adapter, the push button is configured to depress. In response to depression of the push button, the spring may be configured to expand proximally and move the needle hub proximally within the barrel to retract the introducer needle proximally.

The push button may include an opening. The needle hub may extend through the opening. The opening may be keyhole shaped. An edge of the opening may include a first slot and a second slot opposing the first slot. The barrel may include a first protrusion and a second protrusion disposed within the first slot and the second slot, respectively, to inhibit depression of the push button. In response to the push button sliding distally, the first protrusion and the second protrusion may be configured to remove from the first slot and the second slot, respectively, such that the push button is configured to depress when the barrel is spaced apart from the catheter adapter. The first protrusion and the second protrusion may include a wedge shape. The push button may be spaced apart from an edge of the barrel to create a gap between the push button and the barrel when the push button is in the locked position. In response to the push button sliding distally from the locked position to an unlocked position, the push button may close the gap.

According to a third set of embodiments, a catheter system may include a catheter assembly, which may include a catheter adapter. The catheter adapter may include a distal end, a proximal end, and a catheter adapter lumen extending through the distal end of the catheter adapter and the proximal end of the catheter adapter. The catheter system may include a catheter extending from the distal end of the catheter adapter. The catheter system may include a needle assembly, which may include one or more of a barrel, an introducer needle having a sharp distal tip, a needle hub coupled to the introducer needle and movably disposed within the barrel, and a spring disposed within the barrel.

The catheter system may include a push button, which may include an opening and a slot proximate a bottom of the opening. The slot may include a snap protrusion. The needle hub may extend through the opening. The barrel may include a distally-extending pin. The distally-extending pin may be disposed below the snap protrusion. In response to depression of the push button, the pin may snap past the snap protrusion. In response to further depression of the push button, the spring may be configured to expand proximally and move the needle hub proximally within the barrel to retract the introducer needle proximally. The snap protrusion may include a first pair of opposing bumps. The slot may include a second pair of opposing bumps. The distally-extending pin may be disposed between the first pair of opposing bumps and the second pair of opposing bumps.

The push button may include a projection extending in a distal direction. A distal end of the projection may include an arm. The needle hub may include a slot. The arm may be disposed within the slot to inhibit depression of the push button. In response to the further depression of the push button, the arm may be configured to remove from the slot, and the spring may be configured to expand proximally and move the needle hub proximally within the barrel to retract the introducer needle proximally.

According to a fourth set of embodiments, a catheter system may include a catheter assembly, which may include a catheter adapter. The catheter adapter may include a distal end, a proximal end, and a catheter adapter lumen extending through the distal end of the catheter adapter and the proximal end of the catheter adapter. The catheter system may include a catheter extending from the distal end of the catheter adapter. The catheter system may include a needle assembly, which may include one or more of a barrel, an introducer needle having a sharp distal tip, a needle hub coupled to the introducer needle and movably disposed within the barrel, and a spring disposed within the barrel.

The catheter system may include a push button, and in response to movement of the push button, the spring may be configured to expand proximally and move the needle hub proximally within the barrel to retract the introducer needle proximally. A distal face of the push button contacting the barrel may include one or more pads to reduce friction between the push button and the barrel.

According to a fifth set of embodiments, a catheter system may include a catheter assembly, which may include a catheter adapter. The catheter adapter may include a distal end, a proximal end, and a catheter adapter lumen extending through the distal end of the catheter adapter and the proximal end of the catheter adapter. The catheter system may include a catheter extending from the distal end of the catheter adapter. The catheter system may include a needle assembly, which may include one or more of a barrel, an introducer needle having a sharp distal tip, a needle hub coupled to the introducer needle and movably disposed within the barrel, and a spring disposed within the barrel.

The catheter system may include a slider, which may include a groove. A slider rail of the push button may be disposed within the groove and configured to slide within the groove. In a proximal position, the slider may overlap an edge of the barrel to prevent depression of the push button. In response to sliding of the slider from the proximal position to a distal position and the barrel is spaced apart from the catheter adapter, the slider may be configured to depress. In response to depression of the push button, the spring may be configured to expand proximally and move the needle hub proximally within the barrel to retract the introducer needle proximally.

The groove may include a bump. The slider rail may include multiple steps. When the slider is in the proximal position, the bump may be disposed between the steps. In response to sliding of the slider from the proximal position to the distal position, the bump may snap distal to the steps.

It is to be understood that both the foregoing general description and the following detailed description are examples and explanatory and are not restrictive of the invention, as claimed. It should be understood that the various embodiments are not limited to the arrangements and instrumentality illustrated in the drawings. It should also be understood that the embodiments may be combined, or that other embodiments may be utilized and that structural changes, unless so claimed, may be made without departing from the scope of the various embodiments of the present invention. The following detailed description is, therefore, not to be taken in a limiting sense.

BRIEF DESCRIPTION OF THE SEVERAL
VIEWS OF THE DRAWINGS

Example embodiments will be described and explained with additional specificity and detail through the use of the accompanying drawings in which.

DESCRIPTION OF EMBODIMENTS

Figure 1:
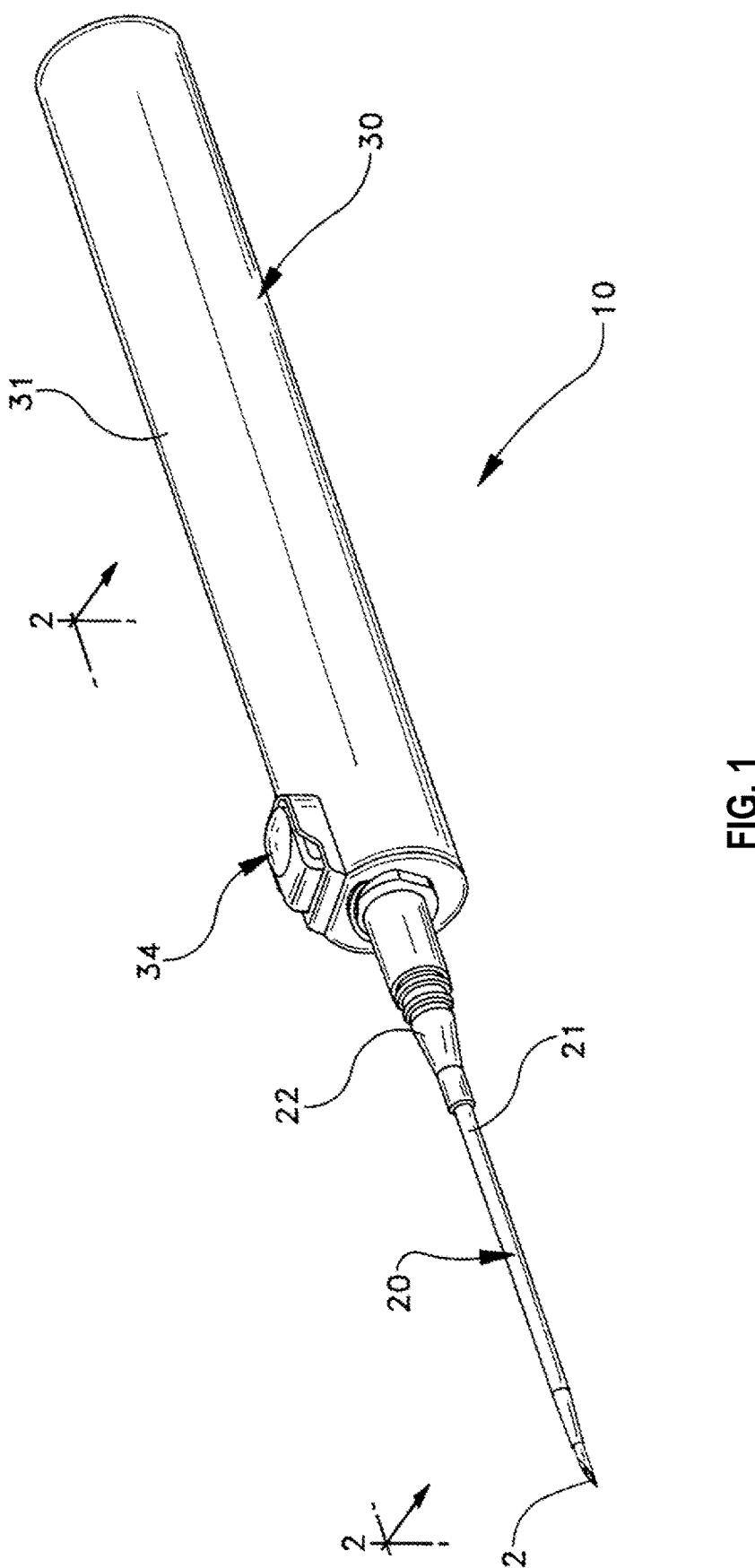
FIG. 1 is an upper perspective view of a prior art catheter system.
Figures 2, 3:
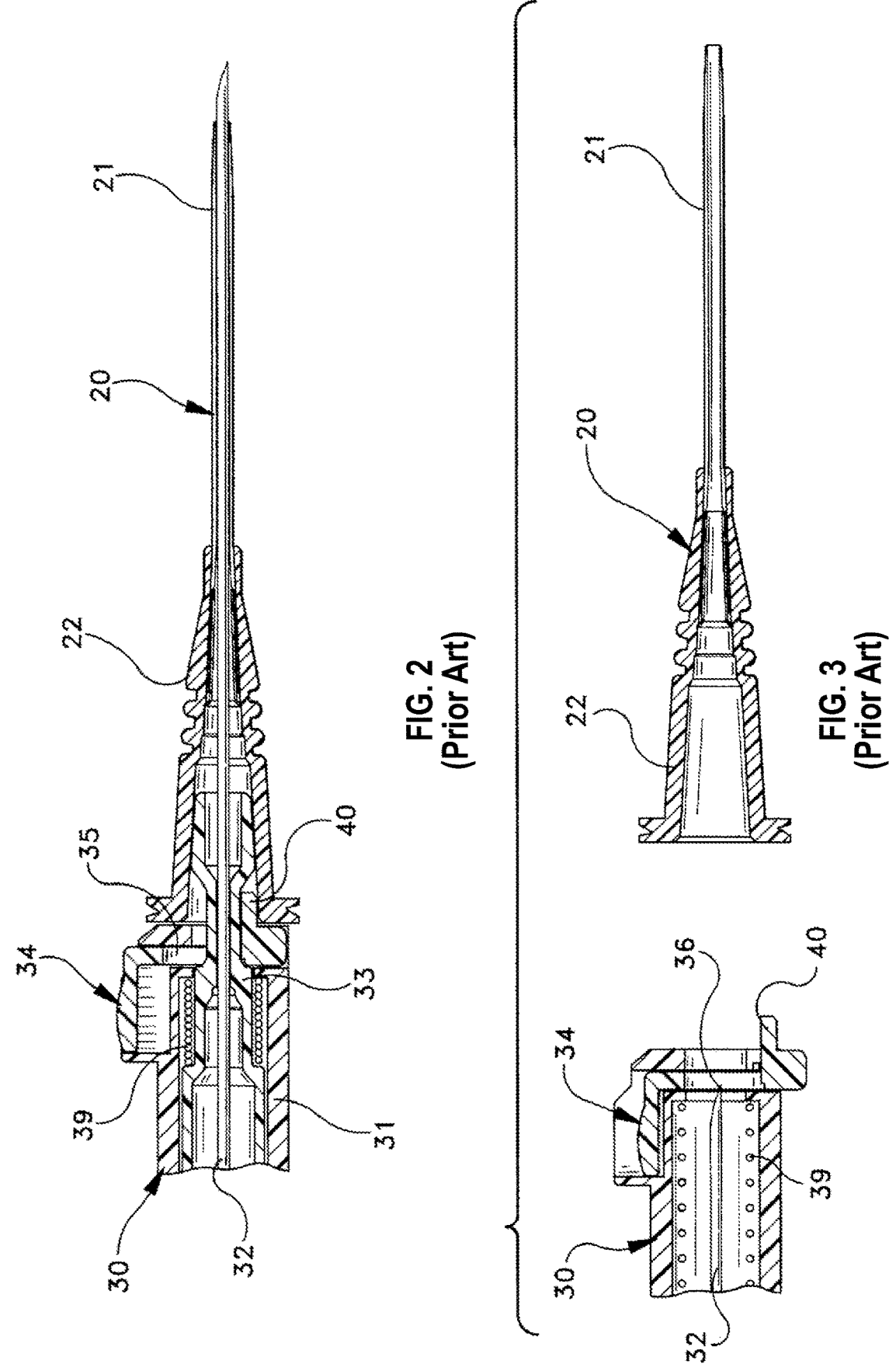
FIG. 2 is a cross-section view taken along line 2-2 of FIG. 1 prior to activation of a spring mechanism.
FIG. 3 is a cross-sectional view of the prior art catheter system similar to the view shown in FIG. 2 but with the catheter advanced distally with respect to an introducer needle assembly and a spring activated and a needle withdrawn into a barrel.
Figure 4:
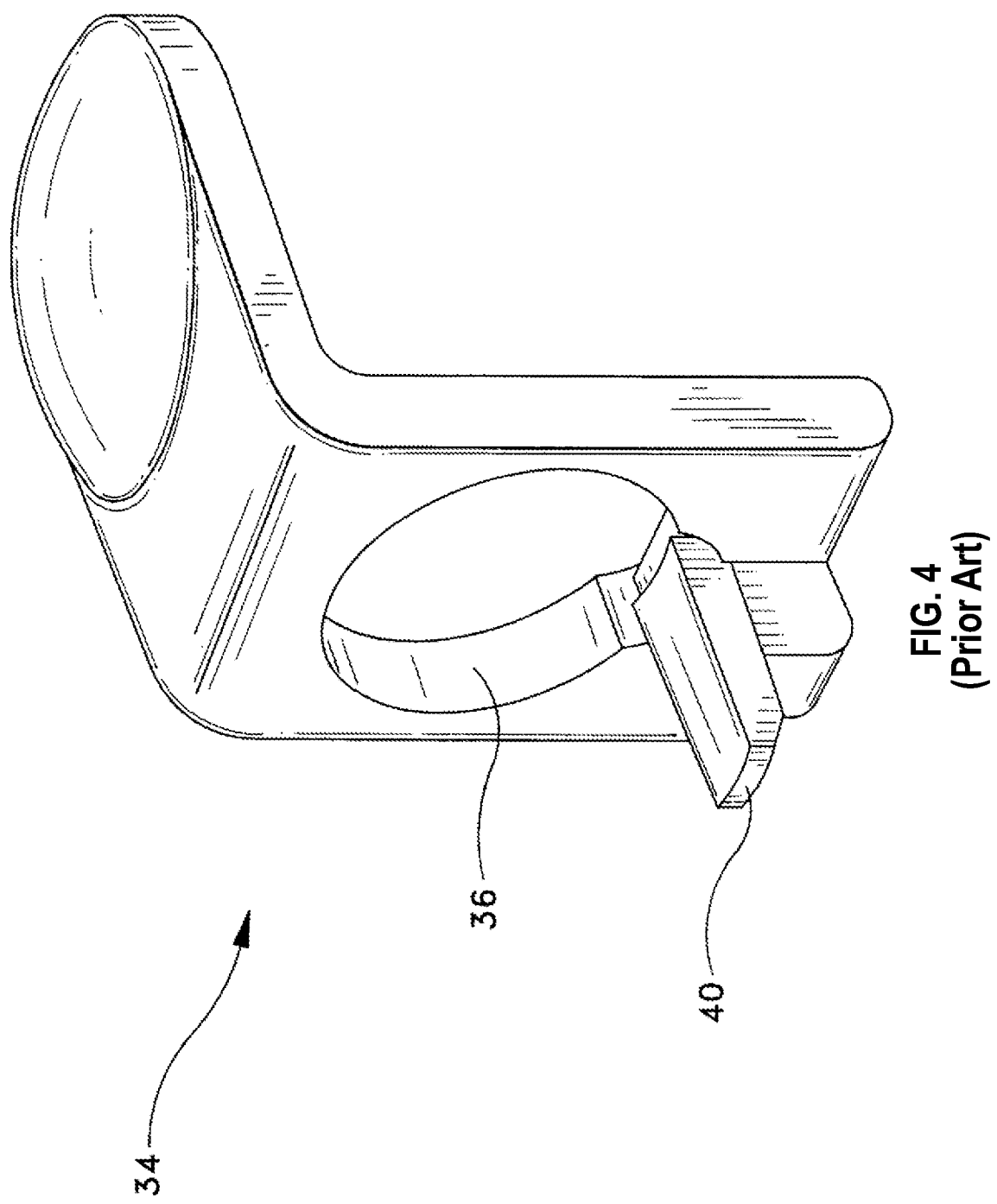
FIG. 4 is an upper perspective view of a push button of the prior art catheter system.

Referring now to FIGS. 1-4, a prior art catheter system 10 is illustrated. A catheter 20 includes a tube 21 which is affixed to a catheter adapter 22. A safety introducer needle assembly 30 includes a handle or barrel 31, a needle 32, a carrier or needle hub 33, a spring 39, and an activation latch or push button 34. The spring 39 is located about the needle 32 and the needle hub 33 and extends between the needle hub 33 and a distal end of barrel 31. The push button 34 extends into the barrel 31 via a slot 35 formed in the barrel 31 adjacent to the distal end. The push button 34 includes a keyhole shaped opening 36 that allows the needle 32 and the needle hub 33 to extend through the push button 34. The push button 34 also includes a projection 40 that extends toward the distal end of catheter 20 and the prior art catheter system 10.

When push button 34 is "up" in the non-activated position, a smaller portion of keyhole shaped opening 36 is in communication with a lumen of the barrel 31. In this position, the smaller opening engages the needle hub 33 and holds the needle hub 33 adjacent to the distal end of barrel 31 against the force of the spring 39. The needle hub 33 has a generally hour-glass shape so that its medial portion has a smaller diameter than either end. This shape facilitates engagement between the smaller opening in keyhole shaped opening 36 of the push button 34 and the needle hub 33. When the push button 34 is in the non-activated position, the projection 40 is located inside the catheter adapter 22. Thus, when the catheter 20 is still located on the needle 32 with the catheter adapter 22 adjacent to the distal end of the barrel 31, the projection 40 prevents the push button 34 from being moved "down" into the activated position. The projection 40 may have a length of between about 0.5 mm and about 2.5 mm. The length used should be long enough so projection 40 engages the catheter adapter 22 when the catheter adapter 22 is adjacent to the distal end of barrel 31. However, the projection 40 should not be so long that it interferes with the use of the catheter 20 and the needle 32.

When the catheter 20 is moved off the needle 32 so the catheter adapter 22 is not adjacent to the distal end of the barrel 31, the push button 34 can be depressed or moved "down," i.e. activated, because the catheter adapter 22 no longer interferes with the movement of the projection 40. In this position, the larger opening of the keyhole shaped opening 36 no longer engages the needle hub 33. The larger opening of the keyhole shaped opening 36 should be larger than the maximum diameter of the needle hub 33. The spring 39 can thus force the needle hub 33 to the proximal end of the barrel 31 and withdraw the sharp distal tip of the needle 32 into the barrel 31.

The projection 40 on the push button 34 can also be angled. This configuration allows a clinician to activate the push button 34 by pressing down firmly on the push button 34. This downward force will transmit some axial force to the catheter adapter 22 because of a wedge shape of the projection. The catheter adapter 22 will then be advanced in the distal direction clearing the way for complete depression of push button 34. The wedge may be at an angle of between about 15 degrees and about 25 degrees to the longitudinal axis of catheter adapter 22. In some embodiments, the push button 34 of the prior art catheter system 10 may operate similar to the activation latch described in U.S. Pat. No. 5,501,675, filed Dec. 27, 1994, entitled "SAFETY CATHETER ASSEMBLY HAVING SAFETY STOP PUSH BUTTON", which is hereby incorporated by reference in its entirety.

Figure 5A:
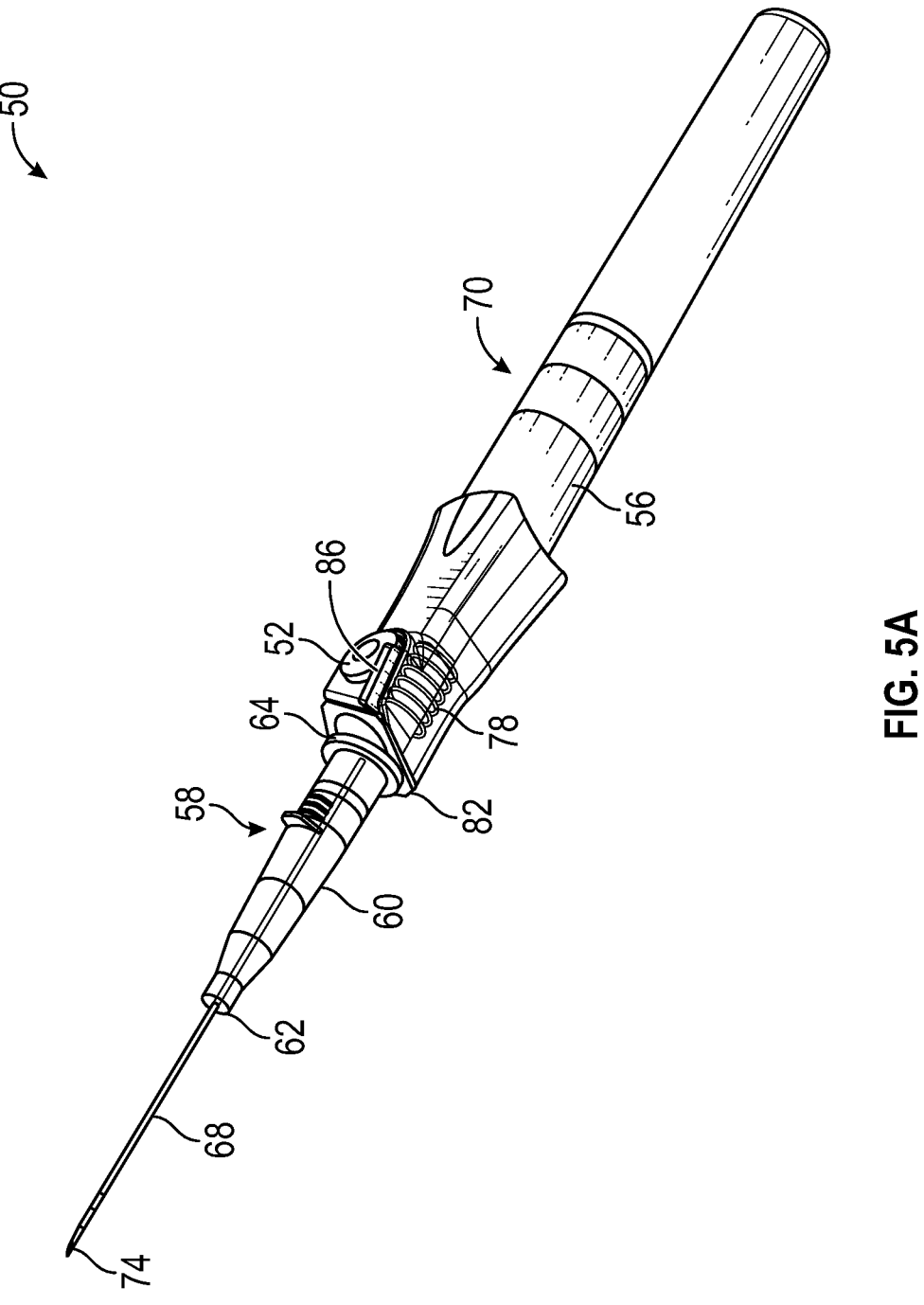
FIG. 5A is an upper perspective view of an example catheter system, according to some embodiments.
Figure 5B:
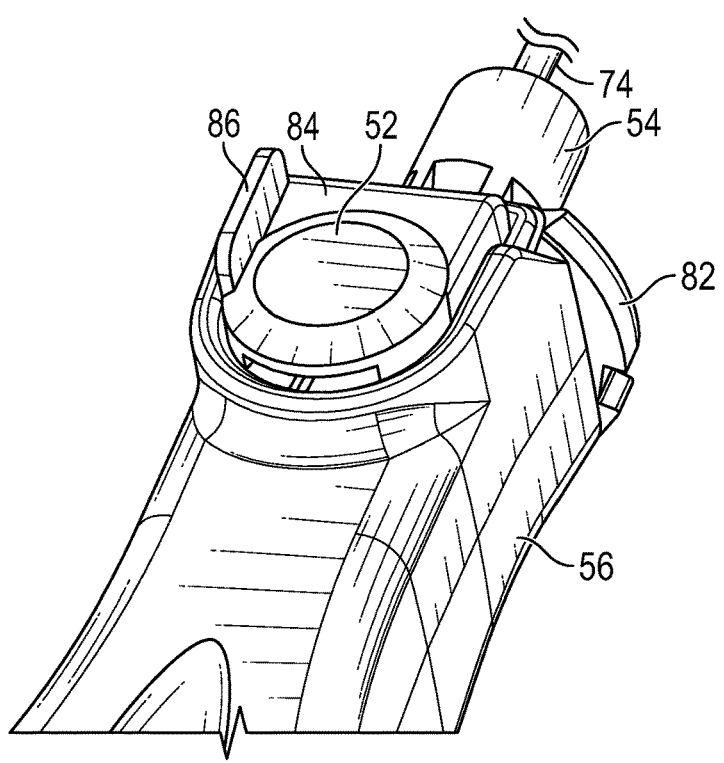
FIG. 5B is an upper perspective view of a portion of the catheter system of FIG. 5A, illustrating an example needle hub spaced apart from an example catheter adapter of the catheter system, according to some embodiments.

Referring now to FIGS. 5A-5K, in some embodiments, a catheter system 50 may be similar or identical to the prior art catheter system 10 of FIGS. 1-4 in terms of one or more features and/or operation. For example, FIG. 5A-5B illustrate a push button 52, a needle hub 54, and a barrel 56, which may be similar or identical to the push button 34, the needle hub 33, and the barrel 31, respectively, of the prior art catheter system 10 of FIGS. 1-4 in terms of one or more features and/or operation, according to some embodiments.

In some embodiments, the catheter system 50 may include a catheter assembly 58, which may include a catheter adapter 60. The catheter adapter 60 may include a distal end 62, a proximal end 64, and a catheter adapter lumen extending through the distal end 62 of the catheter adapter 60 and the proximal end 64 of the catheter adapter 60. The catheter system 50 may include a catheter 68 extending from the distal end 62 of the catheter adapter 60. The catheter system 50 may include a needle assembly 70, which may include one or more of the barrel 56, an introducer needle 74 having a sharp distal tip, the needle hub 54 coupled to the introducer needle 74 and movably disposed within the barrel 56, and a spring 78 disposed within the barrel 56.

In some instances, the catheter 68 may be moved off the needle 32 so the catheter adapter 60 is spaced apart or not adjacent to a distal end 82 of the barrel 31. The catheter system 50 may include the push button 52 disposed in a locked position such that depression of the push button 52 is inhibited or stopped, even when the barrel 56 is spaced apart from the catheter adapter 60. The push button 52 may be configured to slide laterally from the locked position to an unlocked position. In further detail, the push button 52 may slide perpendicular to a longitudinal axis of the catheter system 50. When the push button 52 is in the unlocked position and the barrel 56 is spaced apart from the catheter adapter 60, the push button 52 may be configured to depress. In response to depression of the push button 52, the spring 78 may be configured to expand proximally and move the needle hub 76 proximally within the barrel 56 to retract the introducer needle 74 proximally.

An upper surface 84 of the push button 52 may include a tab 86 generally perpendicular to the longitudinal axis of the catheter system 50. The upper surface 84 of the push button 52 may facilitate lateral sliding of the push button 52. In some embodiments, the tab 86 may be on an edge if the upper surface 84 of the push button 52, which may facilitate placement of a digit of a user on the push button 52 adjacent the tab 86. In some embodiments, the push button 52 may be configured to slide laterally from right to left, as illustrated in FIGS. 5A-5K. In other embodiments, the push button 52 may be configured to slide laterally from left to right.

The push button 52 may include a projection 88, which may extend in a distal direction. A distal end of the projection 88 may include an arm 90. The arm 90 may extend in an opposite direction as a direction of lateral sliding of the push button 52 from the locked position to the unlocked position. The needle hub 54 may include a slot 92. When the push button 52 is in the locked position, the arm 90 may be disposed within the slot 92 to inhibit depression of the push button 52. In response to the push button 52 sliding laterally, the arm 90 may be configured to remove from the slot 92 to facilitate movement of the push button 52 from the locked position to an unlocked position. In some embodiments, when the catheter 68 is moved off the needle 32 so the catheter adapter 60 is not adjacent to the distal end 82 of the barrel 56 and the push button 52 is moved laterally, the push button 52 can be depressed or moved "down," i.e. activated, because the catheter adapter 60 no longer interferes with the movement of the projection 88 and the arm 90 is no longer disposed in the slot 92.

Figure 5C:
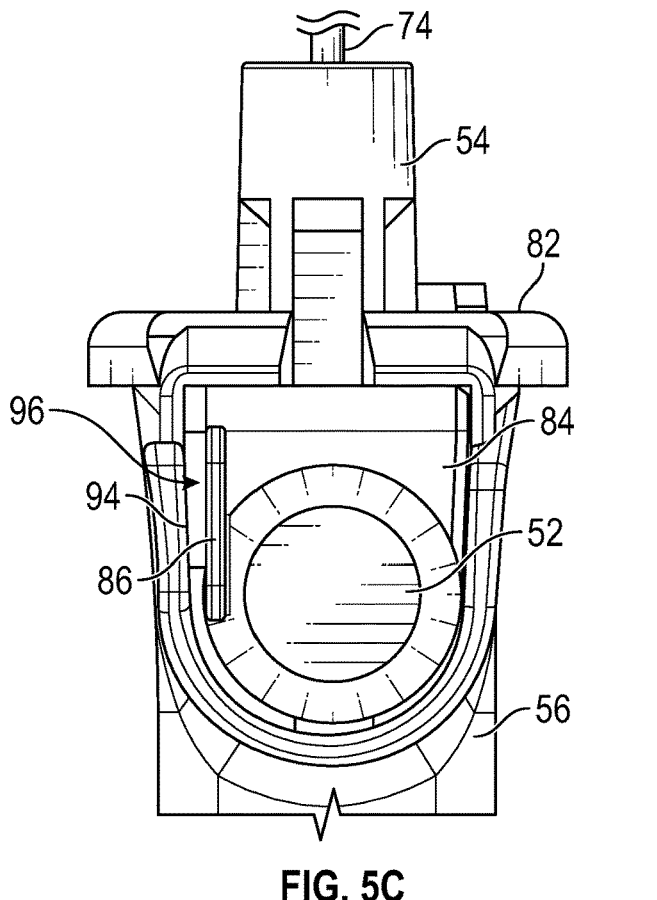
FIG. 5C is top view of a portion of the catheter system of FIG. 5A, illustrating the needle hub spaced apart from the catheter adapter, according to some embodiments.
Figure 5D:
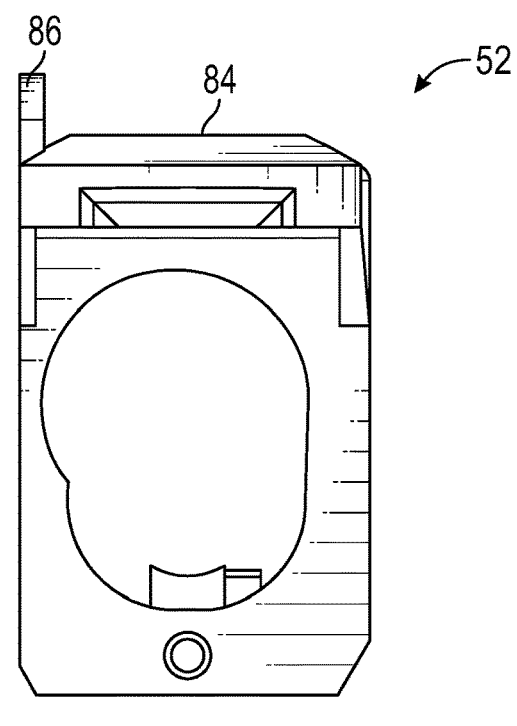
FIG. 5D is a proximal end view of an example push button of the catheter system of FIG. 5A, according to some embodiments.
Figure 5E:
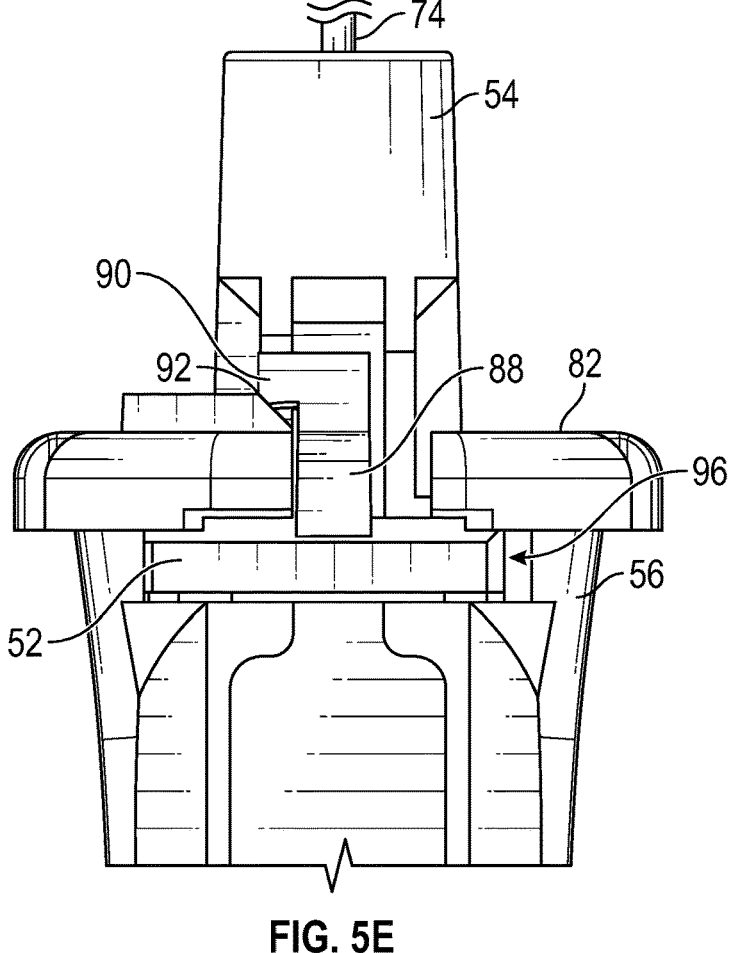
FIG. 5E is a bottom view of a portion of the catheter system of FIG. 5A, illustrating an example arm in an example slot, according to some embodiments.
Figures 5F, 5G:
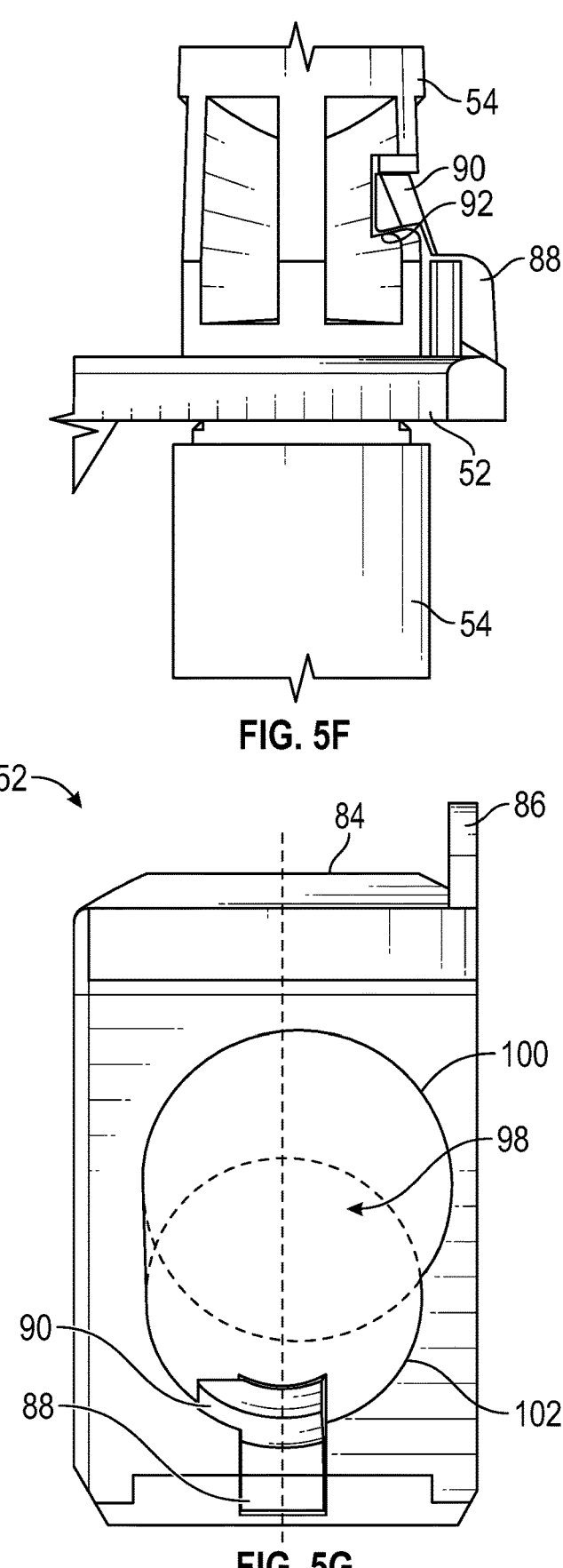
FIG. 5F is a side view of a portion of the catheter system of FIG. 5A, illustrating the arm in the slot, according to some embodiments.
FIG. 5G is a distal end view of the push button of the catheter system of FIG. 5A, according to some embodiments.
Figures 5H, 5I:
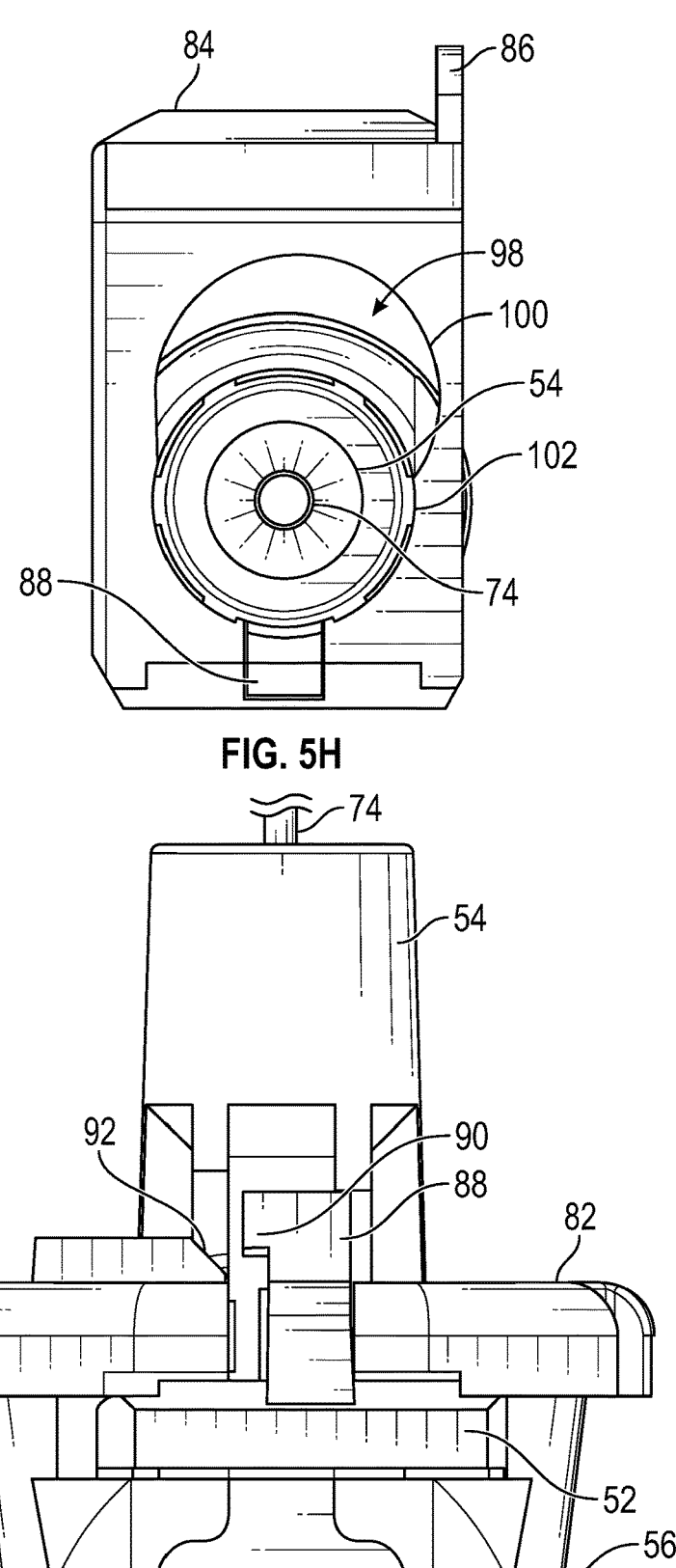
FIG. 5H is a distal end view of the needle hub with the push button in an example locked position, according to some embodiments.
FIG. 5I is a bottom view of a portion of the catheter system of FIG. 5A, illustrating the arm removed from the slot in response to lateral sliding of the push button, according to some embodiments.
Figure 5K:
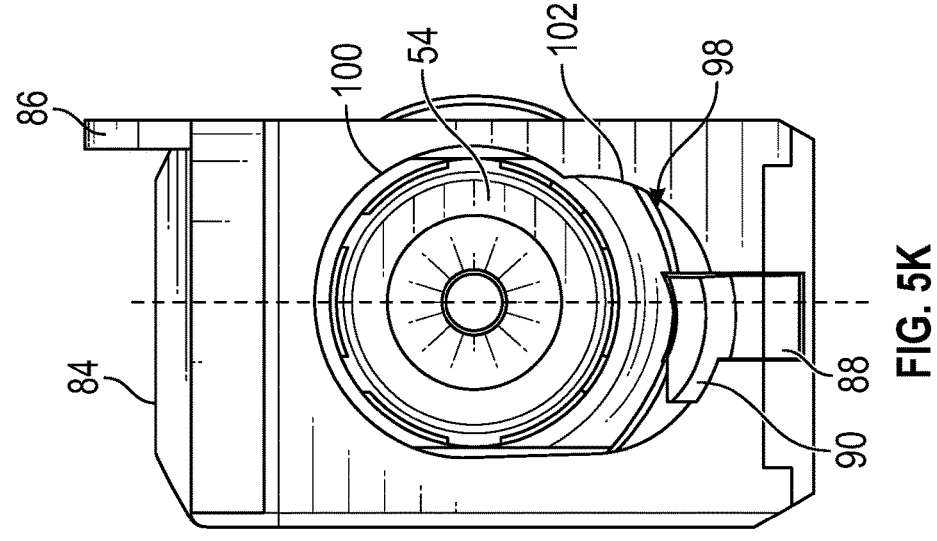
FIG. 5K is a distal end view of the needle hub within the push button in the unlocked position, according to some embodiments.
Figure 5J:
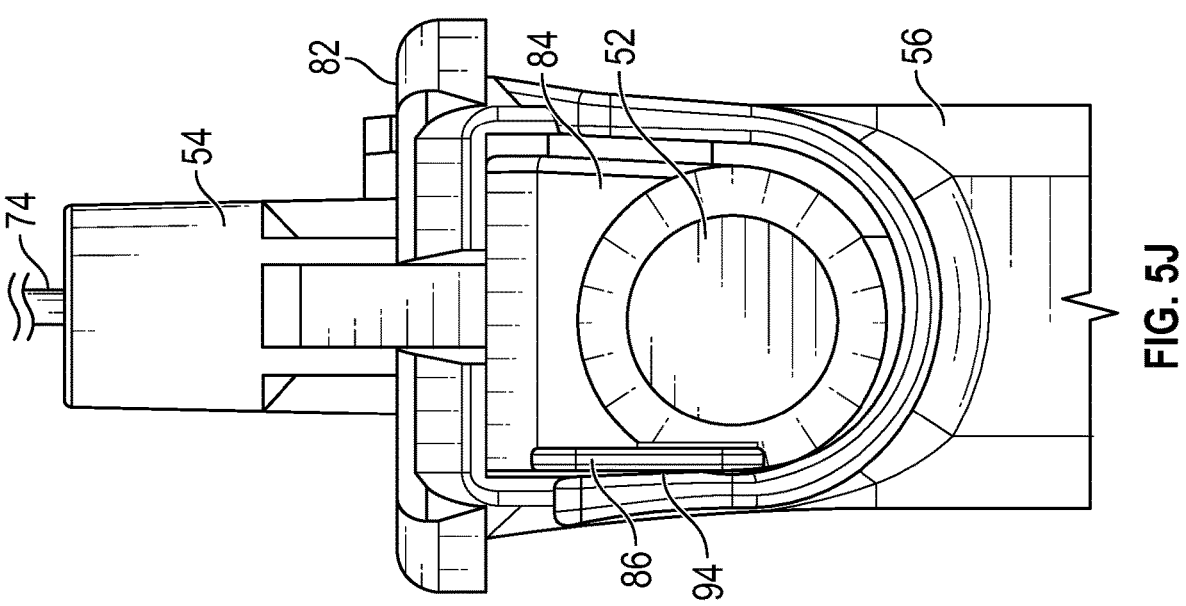
FIG. 5J is a top view of a portion of the catheter system of FIG. 5A, illustrating the push button moved laterally in a left direction to an example unlocked position.

As illustrated in FIG. 5C, for example, the edge of the push button 52 may be spaced apart from an edge 94 of the barrel 56 to a create a gap 96 between the push button 52 and the barrel 56. In response to the push button 52 sliding laterally from the locked position to an unlocked position, the push button 52 may close the gap 96, as illustrated, for example, in FIG. 5K. In response to the push button 52 sliding laterally from the locked position to an unlocked position, a gap may then be created on an opposite of the push button 52 as the gap 96.

The push button 52 may include an opening 98. The needle hub 54 may extend through the opening 98. The opening 98 may include an upper arc 100 proximate a lower arc 102. The upper arc 100 and the lower arc 102 may form half of a keyhole shape. Opposite the half of the keyhole shape, the lower arc 102 may be connected to the upper arc 100 by a straight line. A center of a circle formed by the upper arc 100 may be offset from a center of a circle formed by the lower arc 102. When the push button 52 is in the locked position, the needle hub 54 may be aligned with the center of the circle formed by the lower arc 102. When the push button 52 is in the unlocked position, the needle hub 54 may be aligned with the center of the circle formed by the upper arc 100. The circle formed by the lower arc 102 may be smaller than the circle formed by the upper arc 100. The lower arc 102 may form a smaller portion of the opening 98, and the upper arc 100 may form a larger portion of the opening 98.

A lower portion of the opening 98 including the lower arc 102 may engage the needle hub 54 and hold the needle hub 54 adjacent to the distal end 82 of the barrel 31 against the force of the spring 72. An upper portion of the opening 98 may include a larger diameter than the lower portion of the opening 98. When the push button 52 is moved laterally and then depressed, because the upper portion of the opening 98 is larger than a maximum diameter of the needle hub 54, the spring 72 can thus force the needle hub 54 to a proximal end of the barrel 56 and withdraw the sharp distal tip of the introducer needle 74 into the barrel 56.

Figure 6A:
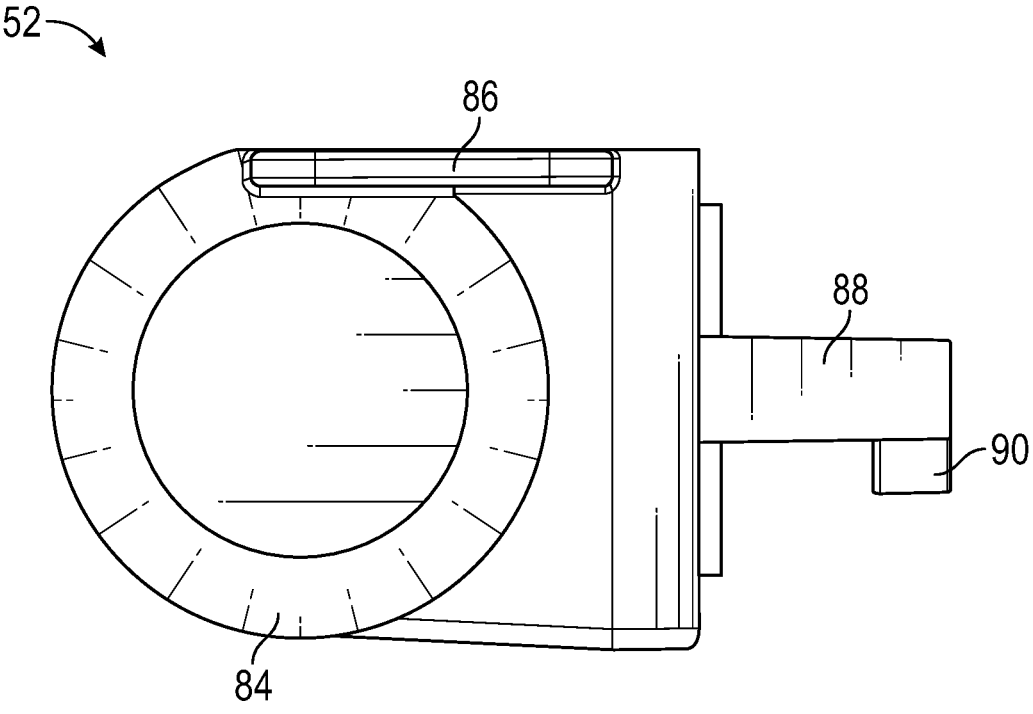
FIG. 6A is a top view of the push button, according to some embodiments.
Figure 6C:
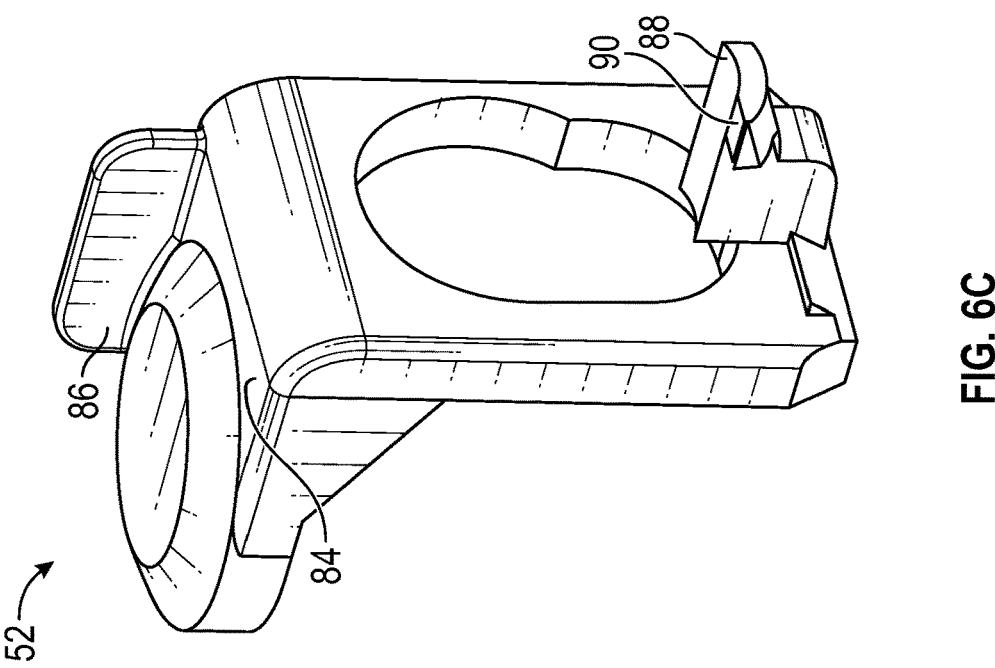
FIG. 6C is an upper perspective view of the push button, according to some embodiments.
Figure 6B:
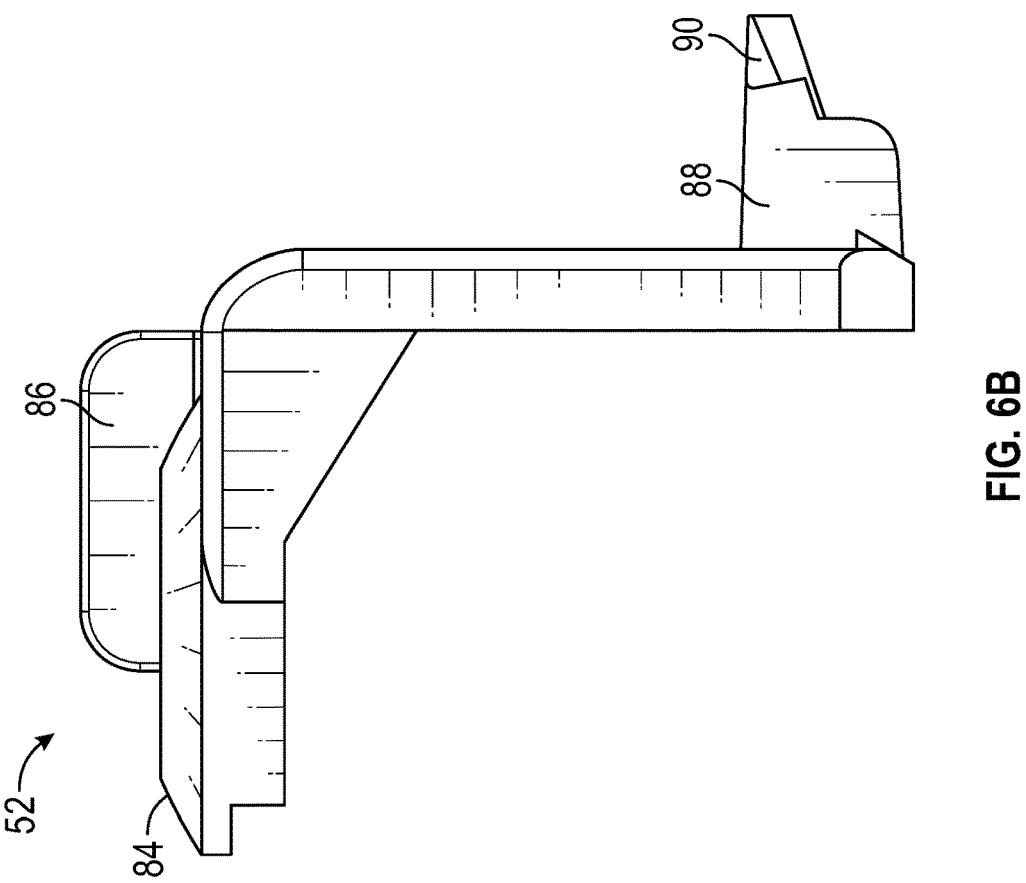
FIG. 6B is a side view of the push button, according to some embodiments.
Figures 6D, 6E, 6F:
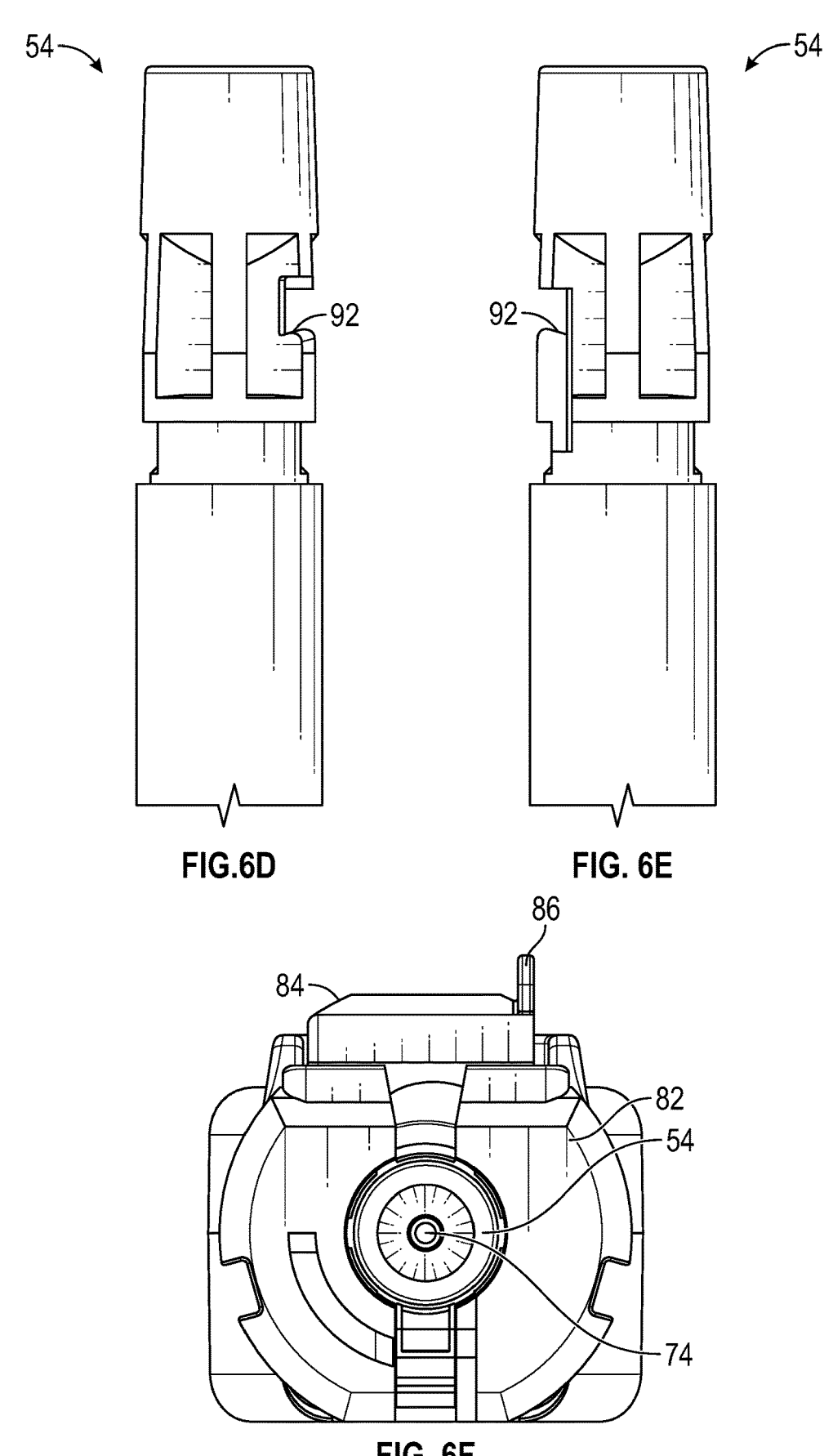
FIG. 6D is a side view of the needle hub, illustrating the slot, according to some embodiments.
FIG. 6E is an opposite side view of the needle hub as FIG. 6D, illustrating the slot, according to some embodiments.
FIG. 6F is a distal end view of the catheter system of FIG. 5A, illustrating the push button in the locked position, according to some embodiments.
Figures 6G, 6H:
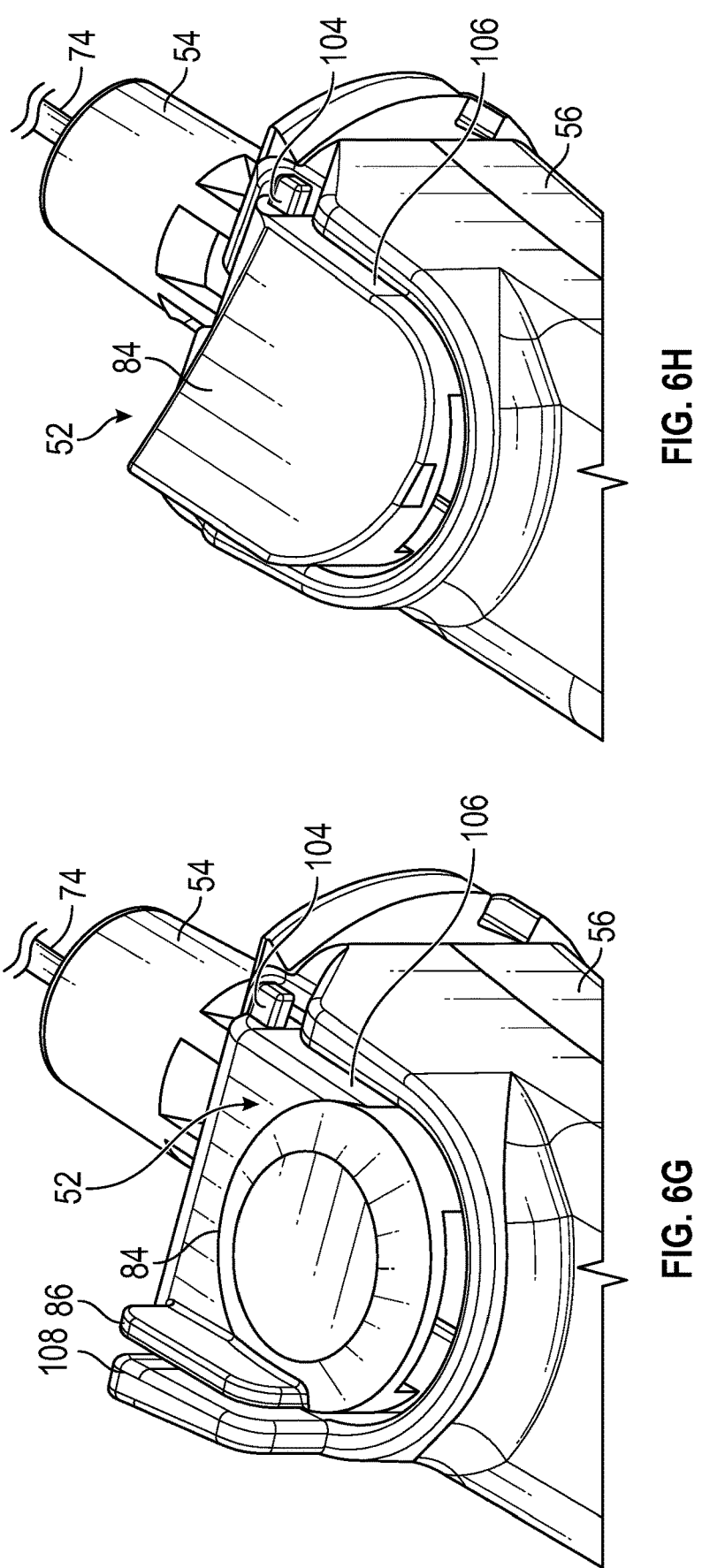
FIG. 6G is an upper perspective view of a portion of the catheter system of FIG. 5A, illustrating an example protrusion, according to some embodiments.
FIG. 6H is an upper perspective view of a portion of the catheter system of FIG. 5A, illustrating an example sloped upper surface of the push button, according to some embodiments.
Figure 7A:
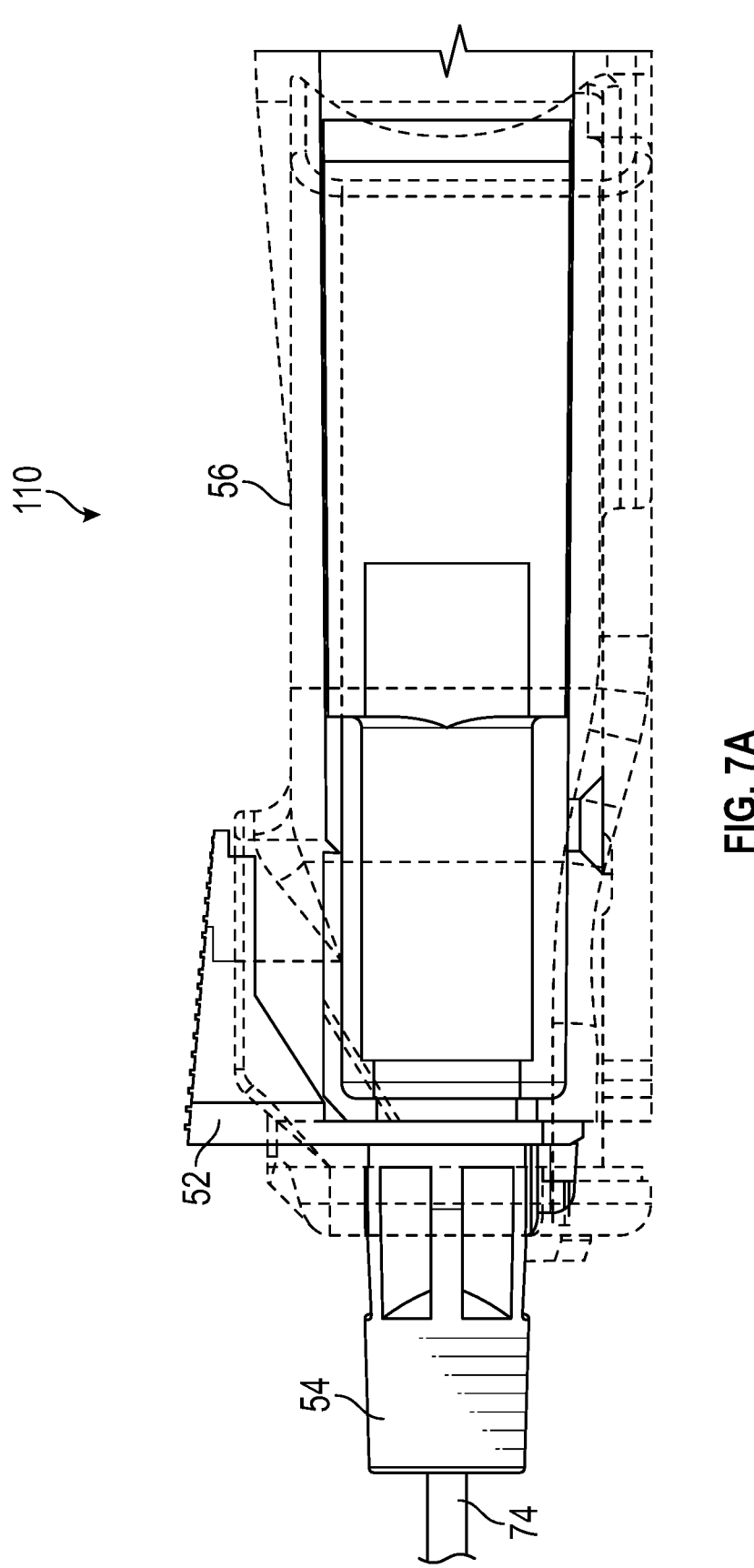
FIG. 7A is a side view of another example catheter system, according to some embodiments.
Figure 7B:
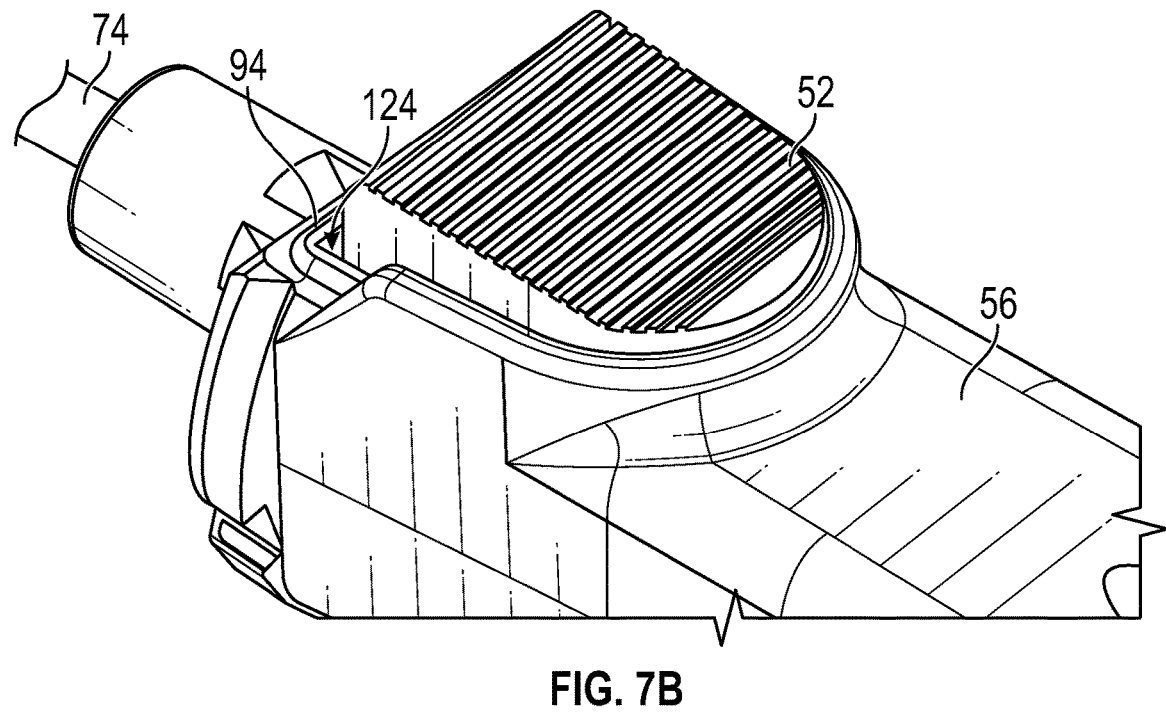
FIG. 7B is an upper perspective view of a portion of the catheter system of FIG. 7A, according to some embodiments.
Figure 7C:
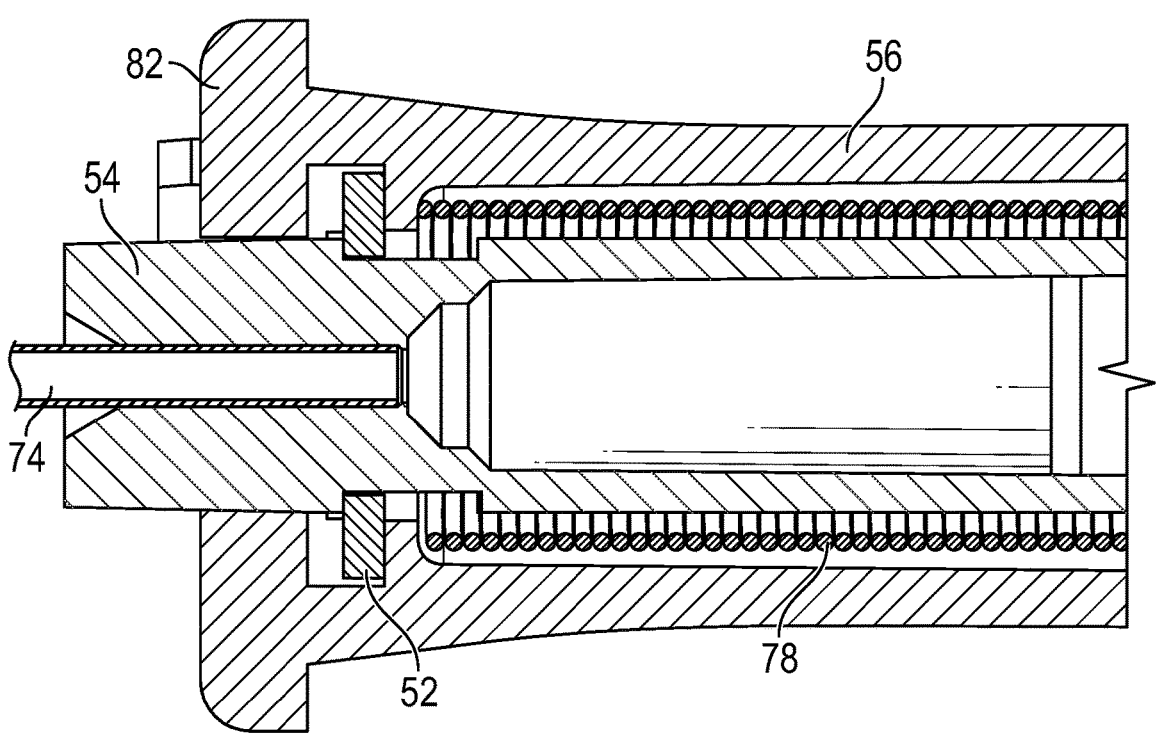
FIG. 7C is a cross-sectional view of a portion of the catheter system of FIG. 7A, according to some embodiments.
Figure 7D:
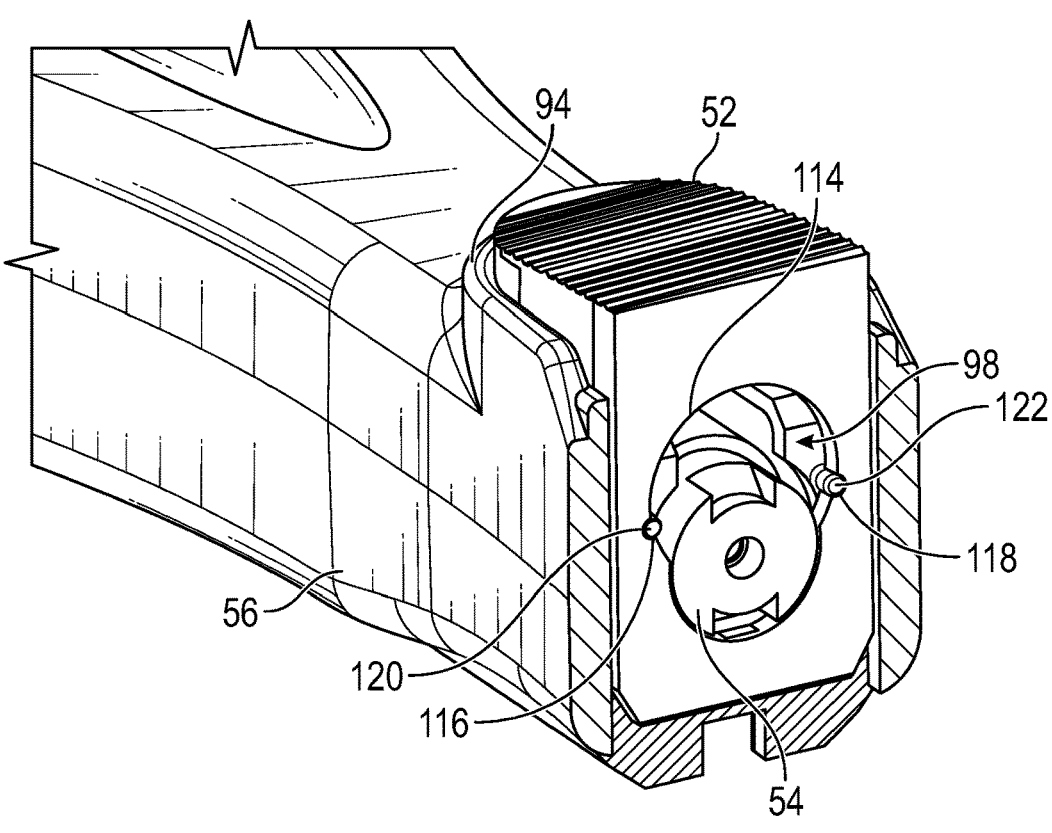
FIG. 7D is a cross-sectional view of a portion of the catheter system of FIG. 7A, with an example introducer needle removed for illustrative purposes, illustrating the push button in an example locked position, according to some embodiments.
Figure 7E:
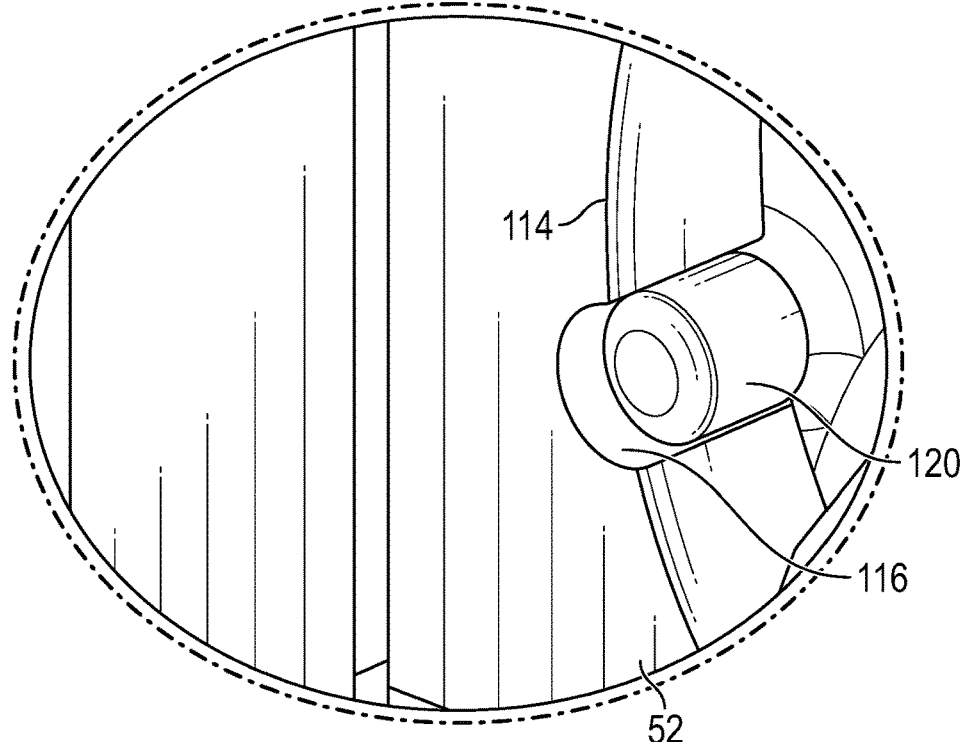
FIG. 7E is an enlarged view of a portion of FIG. 7D, according to some embodiments.
Figure 7F:
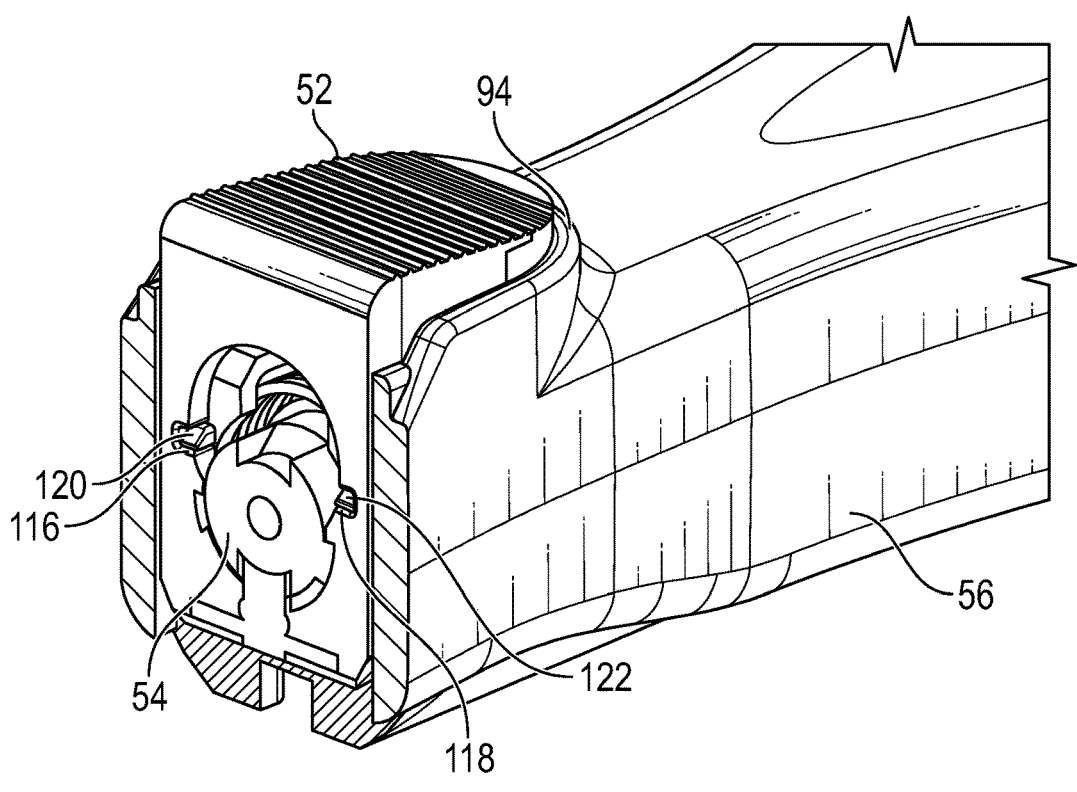
FIG. 7F is a cross-sectional view of a portion of the catheter system of FIG. 7A, with the introducer needle removed for illustrative purposes, illustrating the push button in the locked position, according to some embodiments.
Figure 7G:
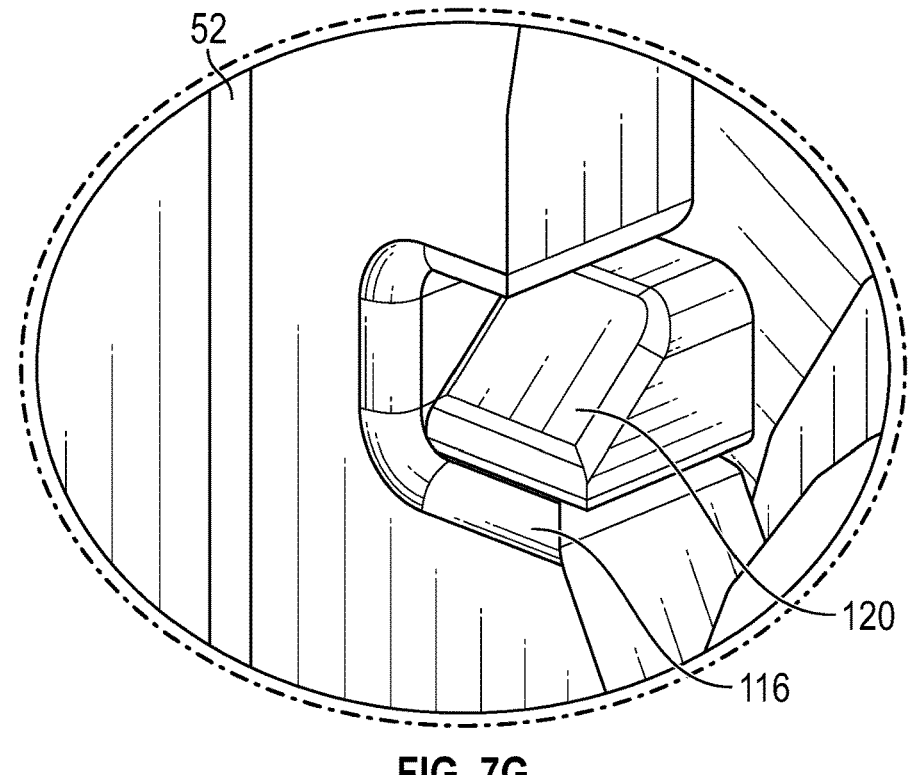
FIG. 7G is an enlarged view of a portion of FIG. 7E, according to some embodiments.
Figure 8A:
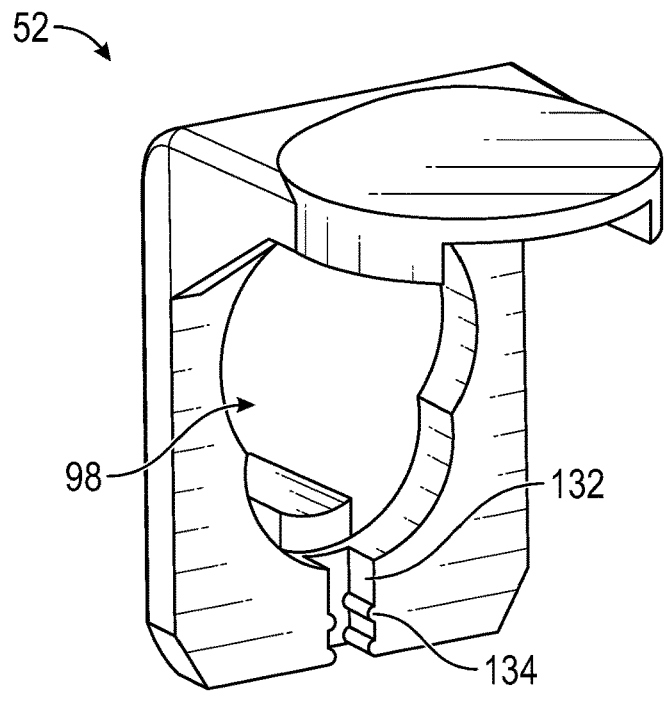
FIG. 8A is an upper perspective view of an example push button, according to some embodiments.
Figure 8B:
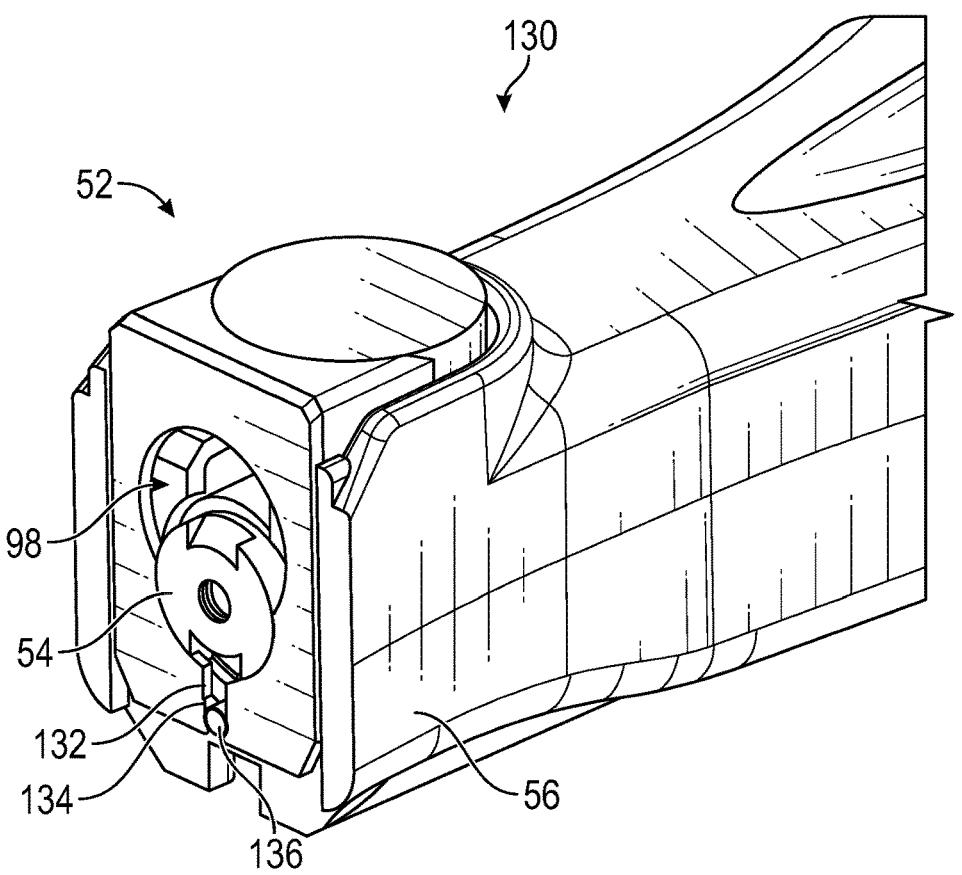
FIG. 8B is a cross-sectional view of another example catheter system, illustrating the push button of FIG. 8A, according to some embodiments.
Figure 8C:
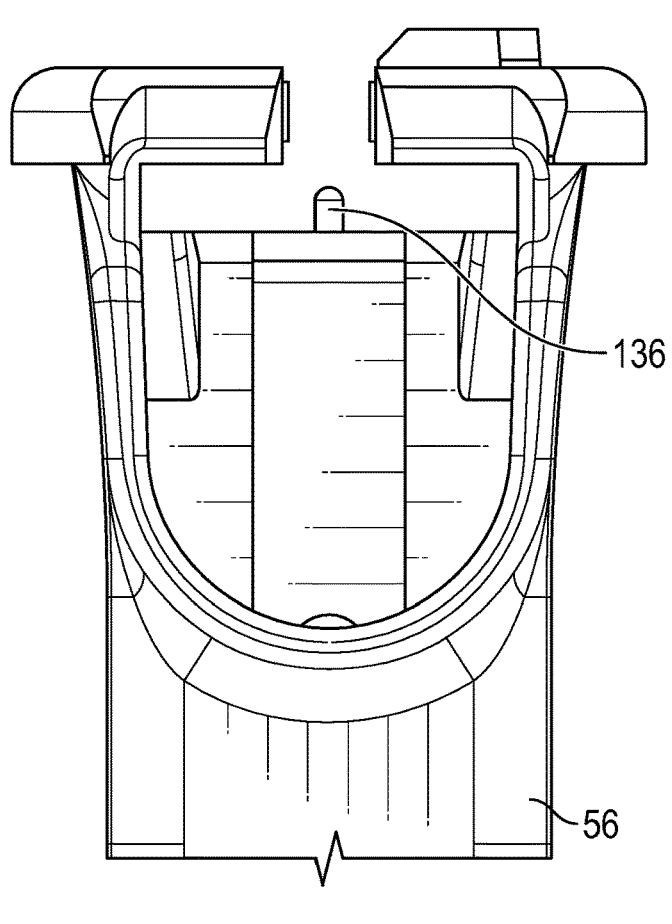
FIG. 8C is a top view of an example barrel, according to some embodiments.
Figure 8D:
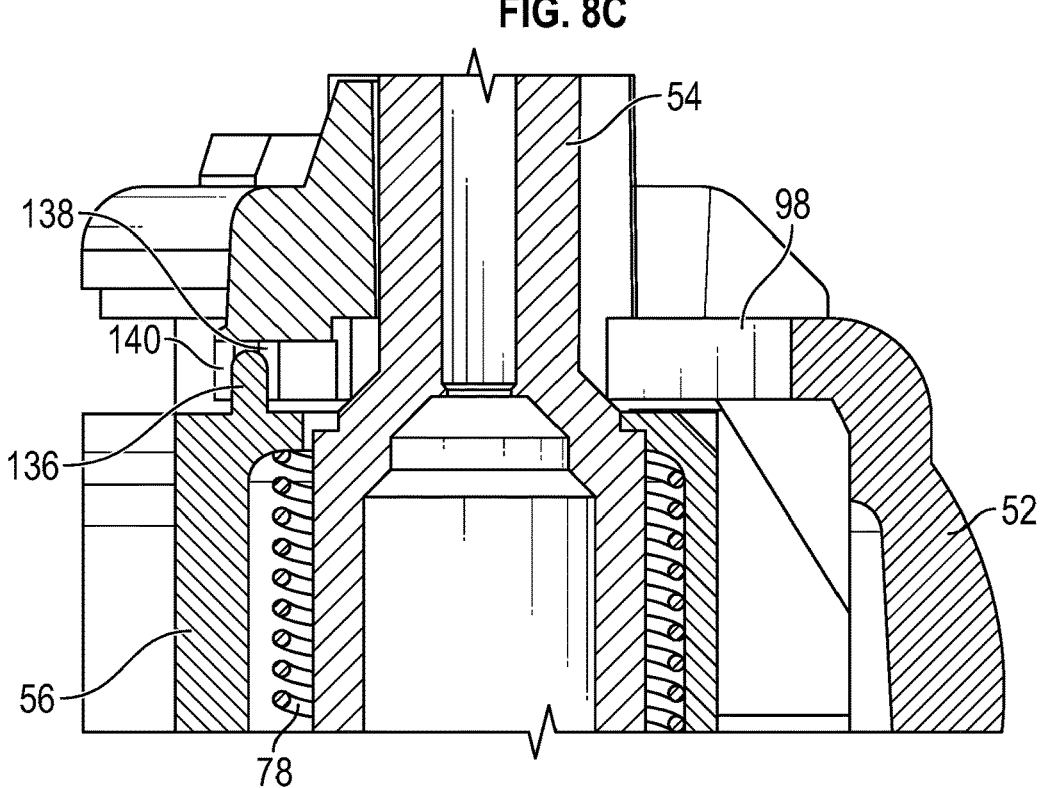
FIG. 8D is a cross-sectional view of a portion of the catheter system of FIG. 8B, with an example introducer needle removed for illustrative purposes, according to some embodiments.
Figure 8E:
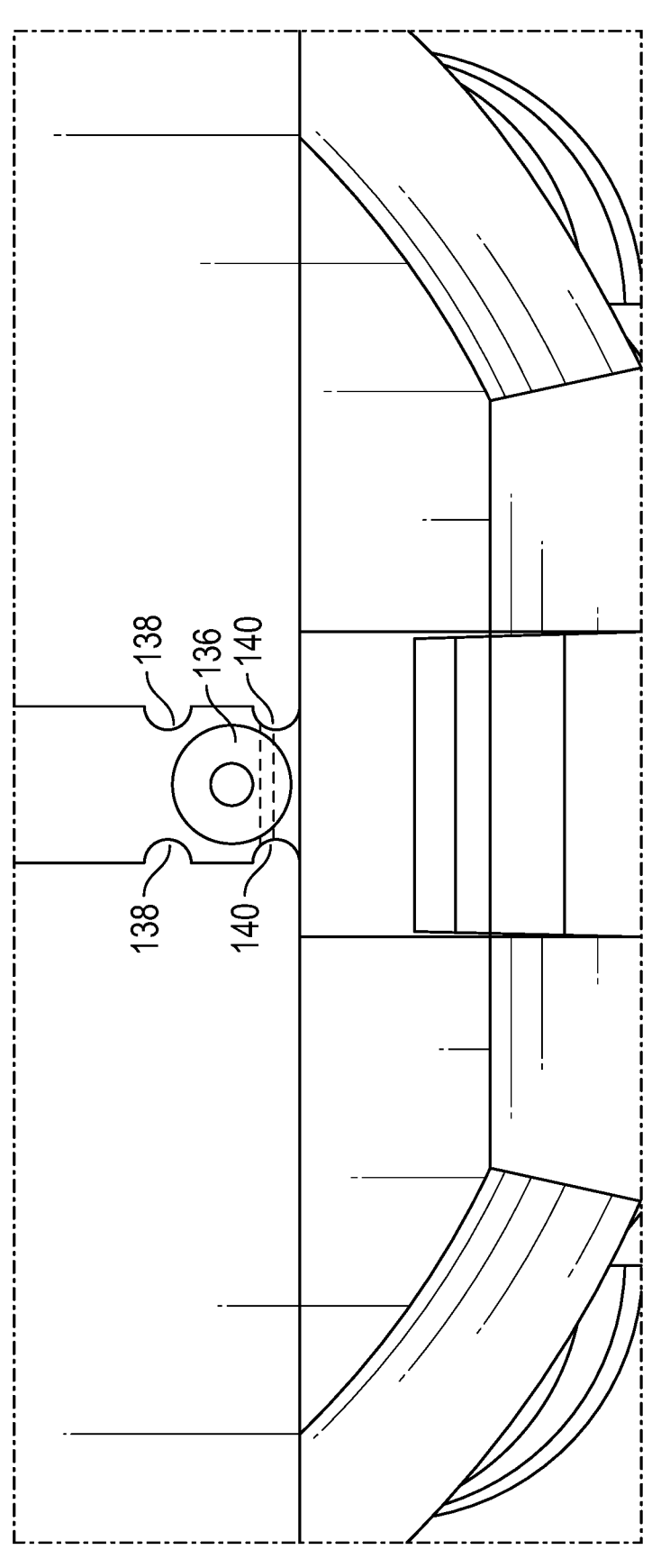
FIG. 8E is a distal end view of a portion of the catheter system of FIG. 8B, according to some embodiments.

Referring now to FIGS. 6A-6H, the push button 52 is illustrated in further detail, according to some embodiments. As illustrated in FIG. 6G, the push button 52 may include a protrusion 104 contacting the edge 94 of the barrel 56 when the push button 52 is in the locked position. In response to the push button 52 sliding laterally from the locked position to the unlocked position, the protrusion 104 may be moved internal to the edge 94 of the barrel 56 such that the push button 52 is configured to depress when the barrel 56 is spaced apart from the catheter adapter 60.

As illustrated in FIG. 6G, the edge 94 may include a tab 108, which may facilitate pinching of the tab 86 and the tab 108 together to slide the push button 52 laterally. In response to sliding of the push button 52 laterally to the unlocked position, the push button 52 may abut the edge 94 and/or the tab 108, which may act as a stop. As illustrated in FIG. 6H, the upper surface 84 of the push button 52 may be sloped upwardly in a direction of lateral sliding of the push button 52 from the locked position to the unlocked position. The upper surface 84 of the push button 52 may facilitate lateral sliding of the push button 52 by a finger of the clinician.

Referring now to FIGS. 7A-7G, a catheter system 110 is illustrated, according to some embodiments. The catheter system 110 may be similar or identical to the prior art catheter system of FIGS. 1-4 and/or the catheter system 50 of FIGS. 5A-5K in terms of one or more features and/or operation. The catheter system 110 may include a push button 52 disposed in a locked position such that depression of the push button is inhibited. The push button 52 may be configured to slide distally from the locked position to an unlocked position. When the push button 52 is in the unlocked position and the barrel 56 is spaced apart from the catheter adapter 60, the push button 52 may be configured to depress. In response to depression of the push button 52, the spring 78 may be configured to expand proximally and move the needle hub 54 proximally within the barrel 56 to retract the introducer needle 74 proximally.

The push button may include an opening 98, and the needle hub 54 may extend through the opening 98. The opening 98 may be keyhole shaped. An edge 114 of the opening 98 may include a first slot 116 and a second slot 118 opposing the first slot 116. The barrel 56 may include a first protrusion 120 and a second protrusion 122 disposed within the first slot 116 and the second slot 118, respectively, to inhibit depression of the push button 52. In response to the push button 52 sliding distally, the first protrusion 120 and the second protrusion 122 may be configured to remove from the first slot 116 and the second slot 118, respectively, such that the push button 52 is configured to depress when the barrel 56 is spaced apart from the catheter adapter 60. The first protrusion 120 and the second protrusion 122 may include a wedge shape. A distal face of the wedge may be tapered or have a slope to facilitate motion of the push button 52 in a same or similar direction as the slope.

The push button 52 may be spaced apart from an edge 94 of the barrel 56 to create a gap 124 between the push button 52 and the barrel 56 when the push button 52 is in the locked position. In response to the push button 52 sliding distally from the locked position to an unlocked position, the push button 52 may close the gap 124. In response to sliding of the push button 52 distally to the unlocked position, the push button 52 may abut the edge 94, which may act as a stop.

Referring now to FIGS. 8A-8E, a catheter system 130 is illustrated, according to some embodiments. The catheter system 130 may be similar or identical to one or more of the prior art catheter system 10 of FIGS. 1-4, the catheter system 50 of FIGS. 5A-5K, and the catheter system 110 of FIGS. 7A-7G in terms of one or more features and/or operation. The catheter system 130 may include a push button 52, which may include an opening 98 and a slot 132 proximate a bottom of the opening 98. The slot 132 may include a snap protrusion 134. The needle hub 54 may extend through the opening 98. The barrel 56 may include a distally-extending pin 136. The distally-extending pin 136 may be disposed below the snap protrusion 134. In response to depression of the push button 52, the distally-extending pin 136 may snap past the snap protrusion 134. In response to further depression of the push button 52, the spring 78 may be configured to expand proximally and move the needle hub 54 proximally within the barrel 56 to retract the introducer needle 74 (see, for example, FIG. 7C) proximally. The snap protrusion 134 may include a first pair of opposing bumps 138. The slot 132 may include a second pair of opposing bumps 140. The distally-extending pin 136 may be disposed between the first pair of opposing bumps 138 and the second pair of opposing bumps 140, which may secure the push button 52.

Figure 9A:
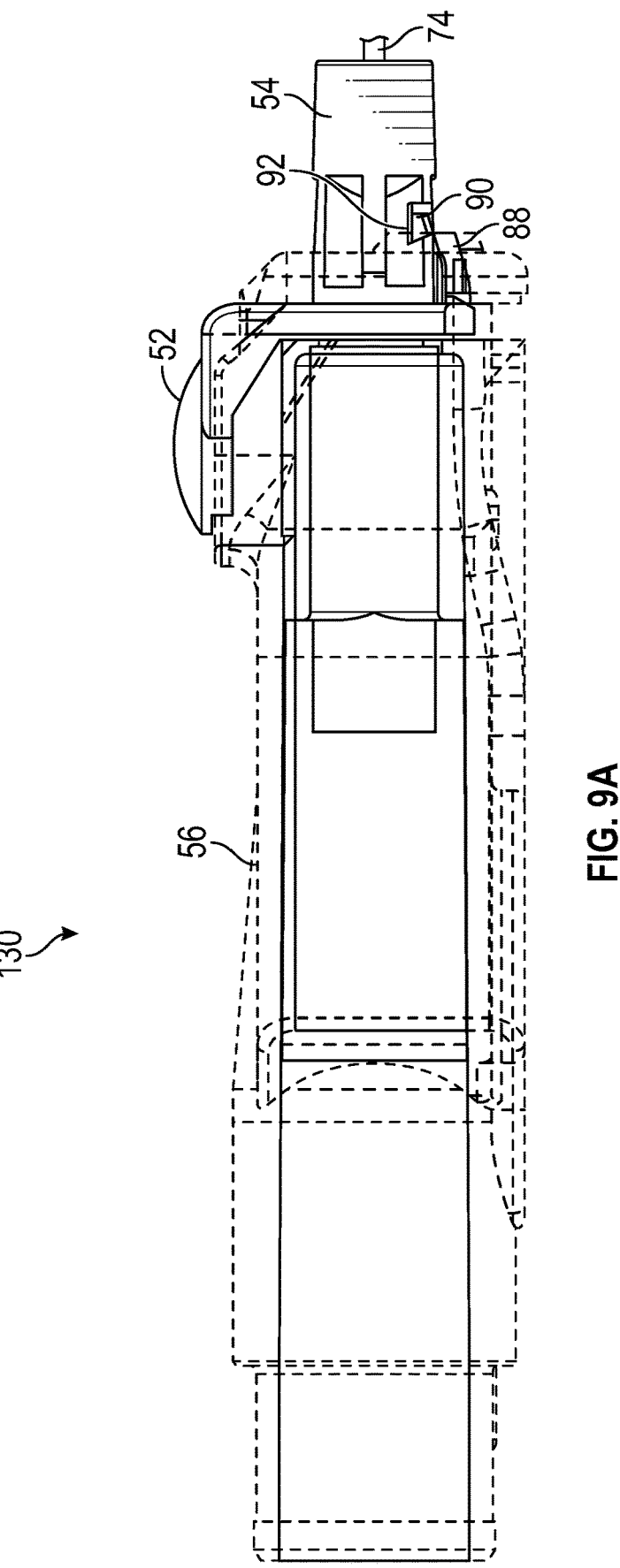
FIG. 9A is a side view of a portion of the catheter system of FIG. 8B, according to some embodiments.
Figure 9B:
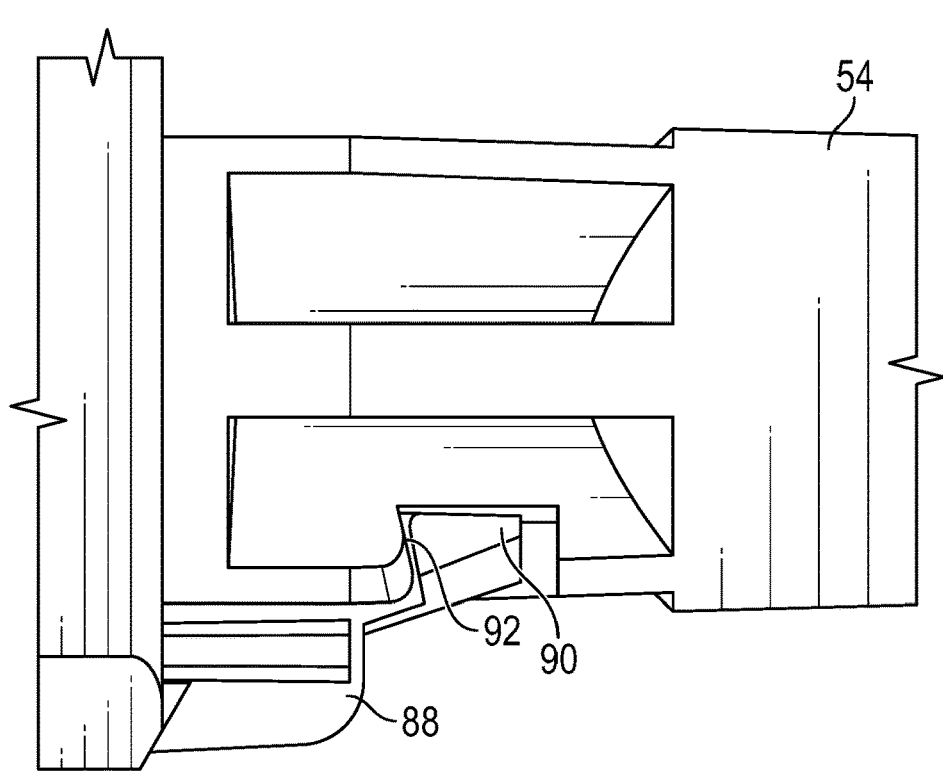
FIG. 9B is a side view of the needle hub, illustrating the slot, according to some embodiments.

Referring now to FIGS. 9A-9B, the push button 52 may include the projection 88 or snap beam extending in a distal direction. A distal end of the projection may include the arm 90. The needle hub 54 may include the slot 92. The arm 90 may be disposed within the slot 92 to inhibit depression of the push button 52. Pushing of the push button 52 may make the projection 88 to bend and release from the slot 92, which may produce an audible click. The projection 88 may bend and release from the slot 92 followed by the distally-extending pin 136 snapping past the snap protrusion 134, which may also result in an audible click. In response to the further depression of the push button 52, the spring 78 may be configured to expand proximally and move the needle hub 54 proximally within the barrel 56 to retract the introducer needle 74 proximally.

Figure 9C:
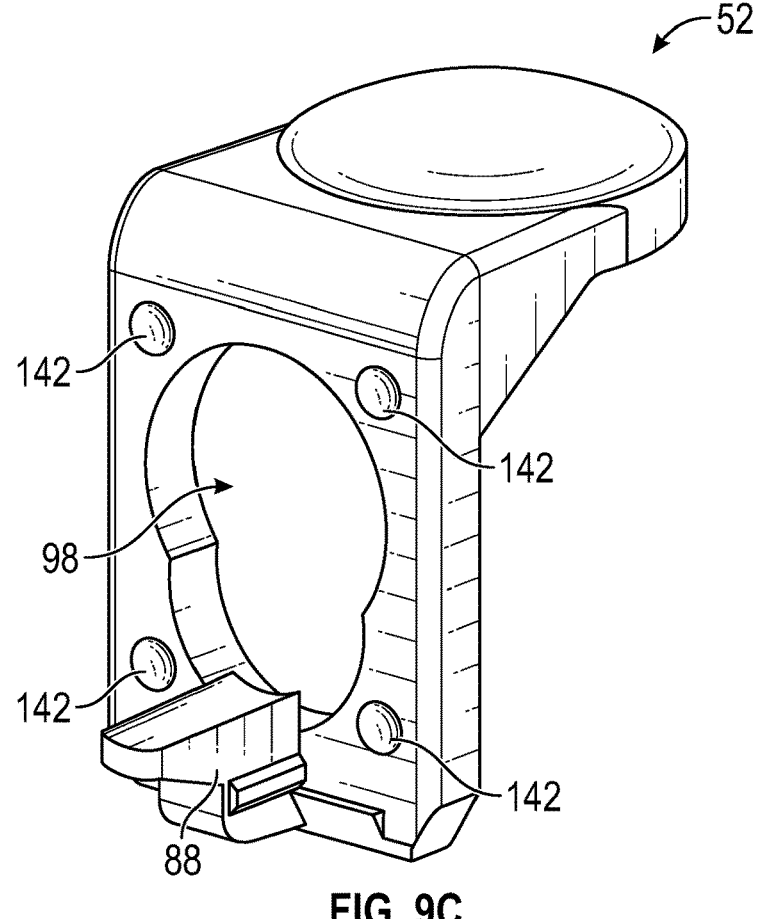
FIG. 9C is an upper perspective view of an example push button, according to some embodiments.
Figure 9D:
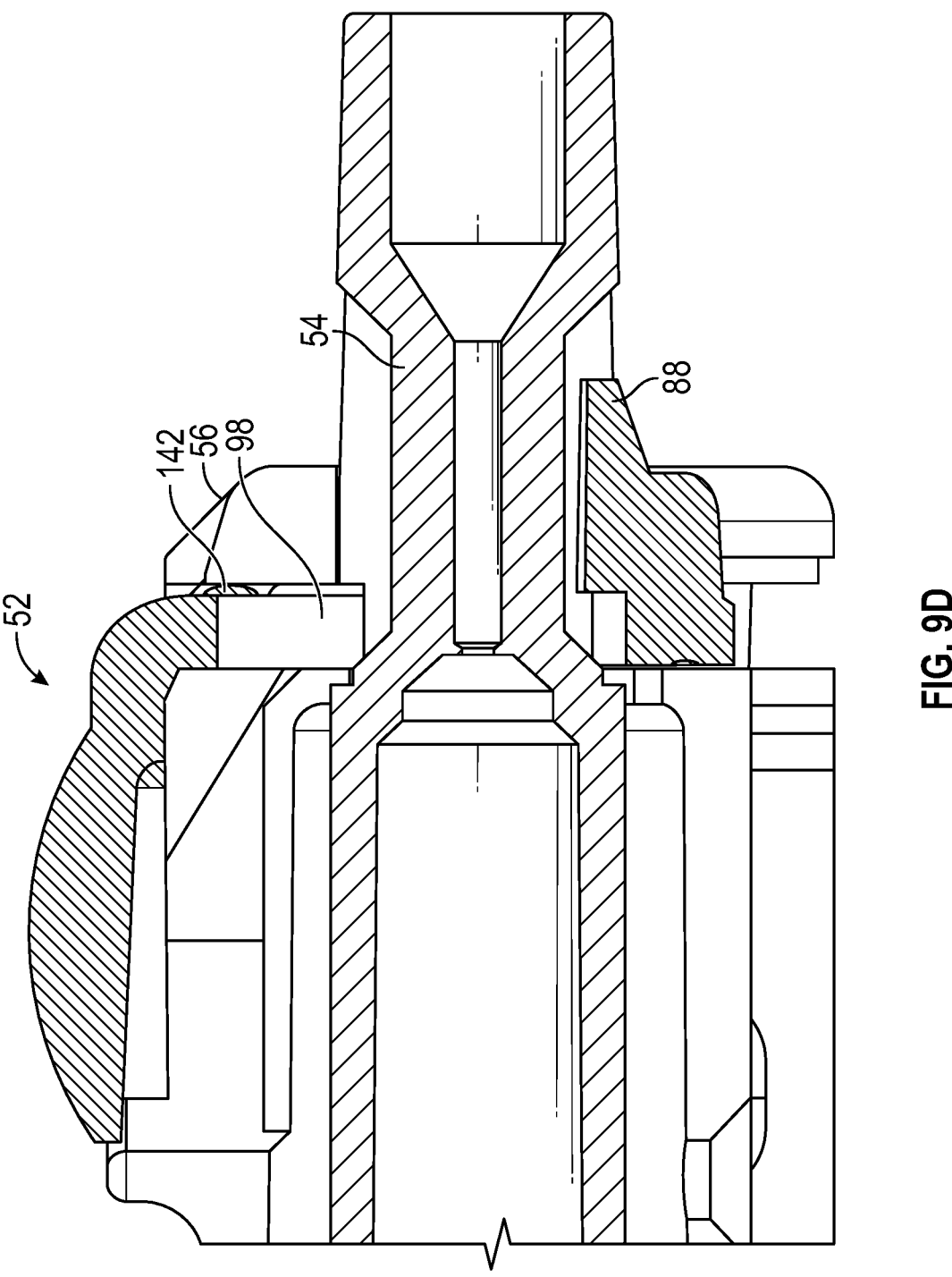
FIG. 9D is a cross-sectional view of an example catheter system, illustrating the push button of FIG. 9C, according to some embodiments.
Figure 10A:
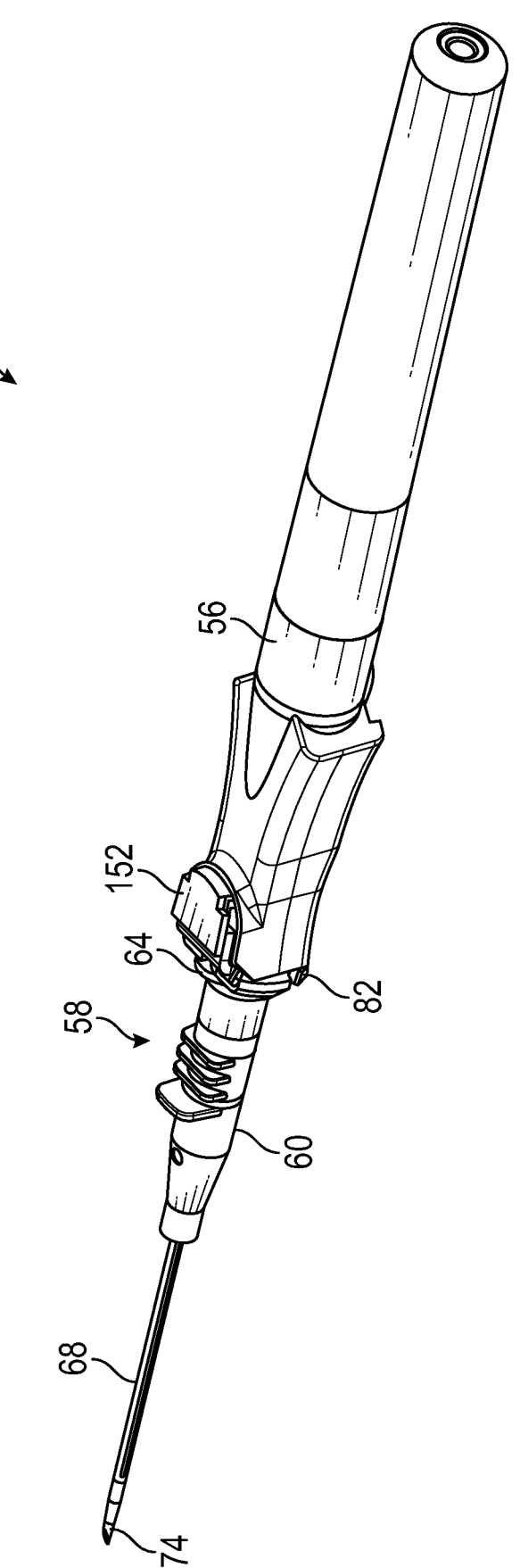
FIG. 10A is an upper perspective view of another example catheter system, according to some embodiments.
Figure 10B:
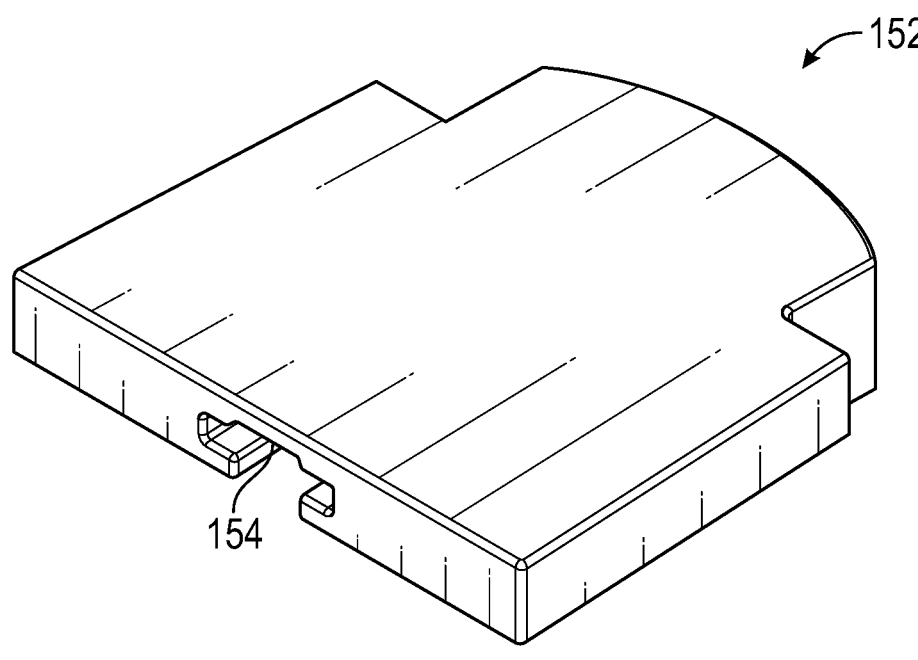
FIG. 10B is an upper perspective view of an example slider, according to some embodiments.
Figure 10C:
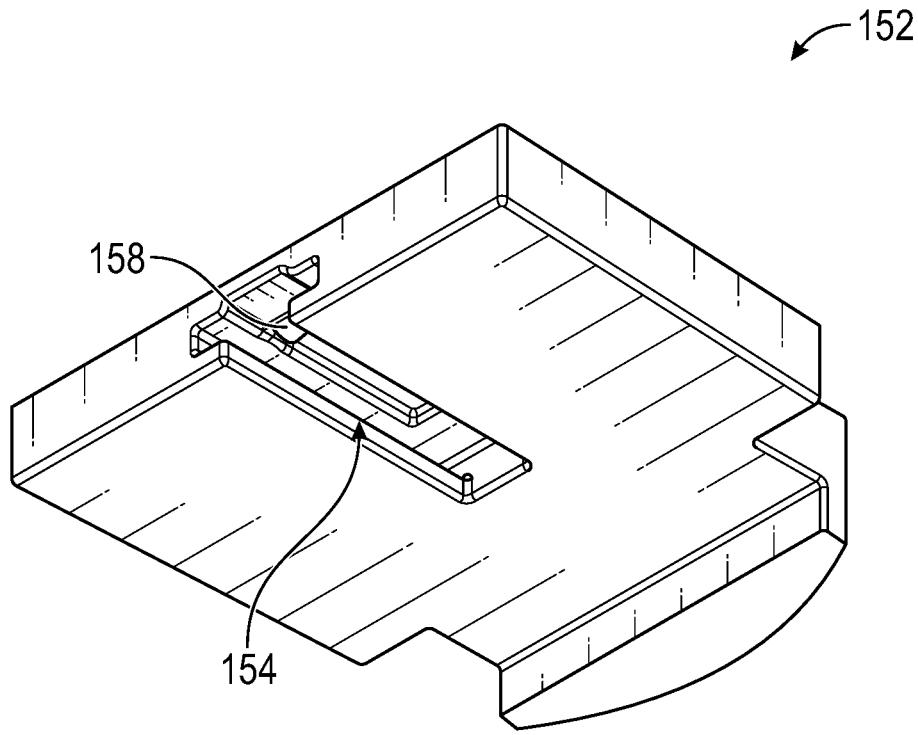
FIG. 10C is a lower perspective view of the slider, according to some embodiments.
Figure 10D:
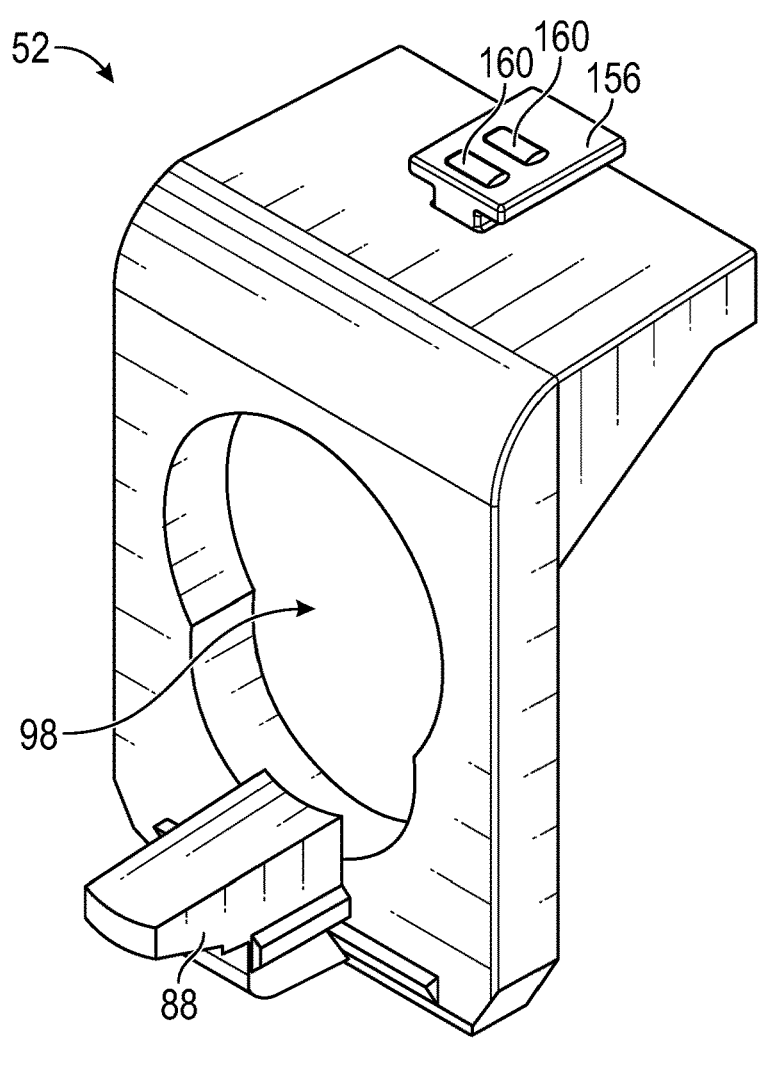
FIG. 10D is an upper perspective view of an example push button of the catheter system of FIG. 10A, according to some embodiments.
Figure 10E:
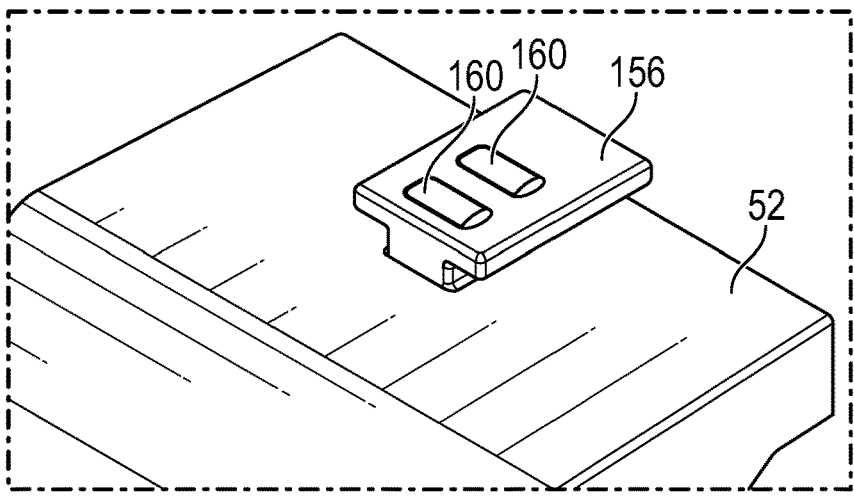
FIG. 10E is an enlarged view of a portion of FIG. 10D, according to some embodiments.
Figure 11A:
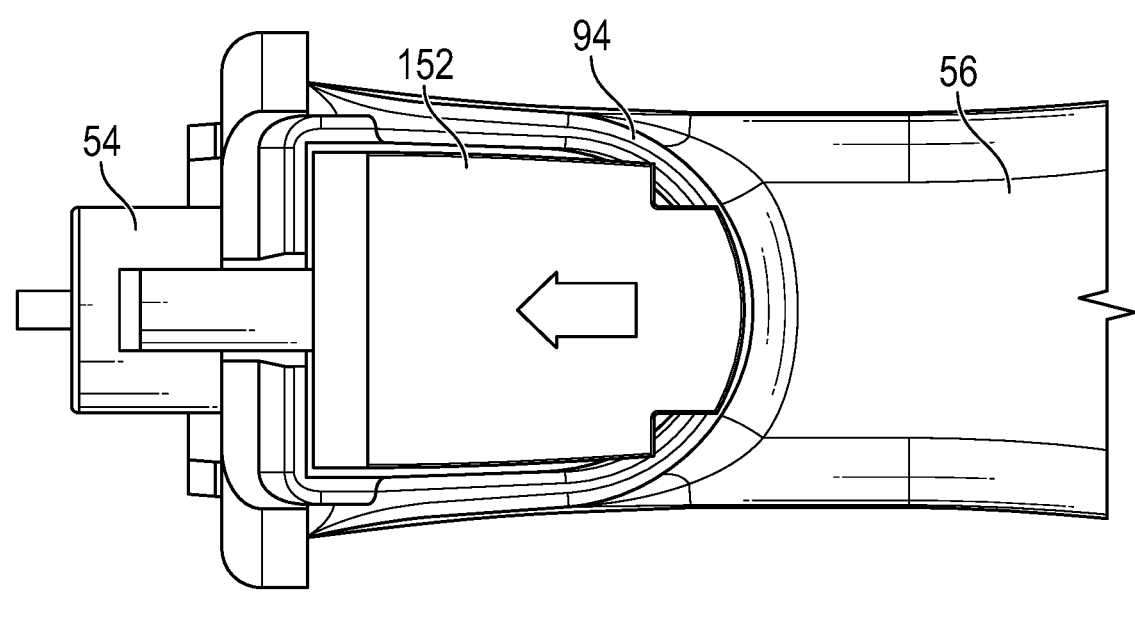
FIG. 11A is a top view of a portion of the catheter system of FIG. 10A, according to some embodiments.
Figure 11B:
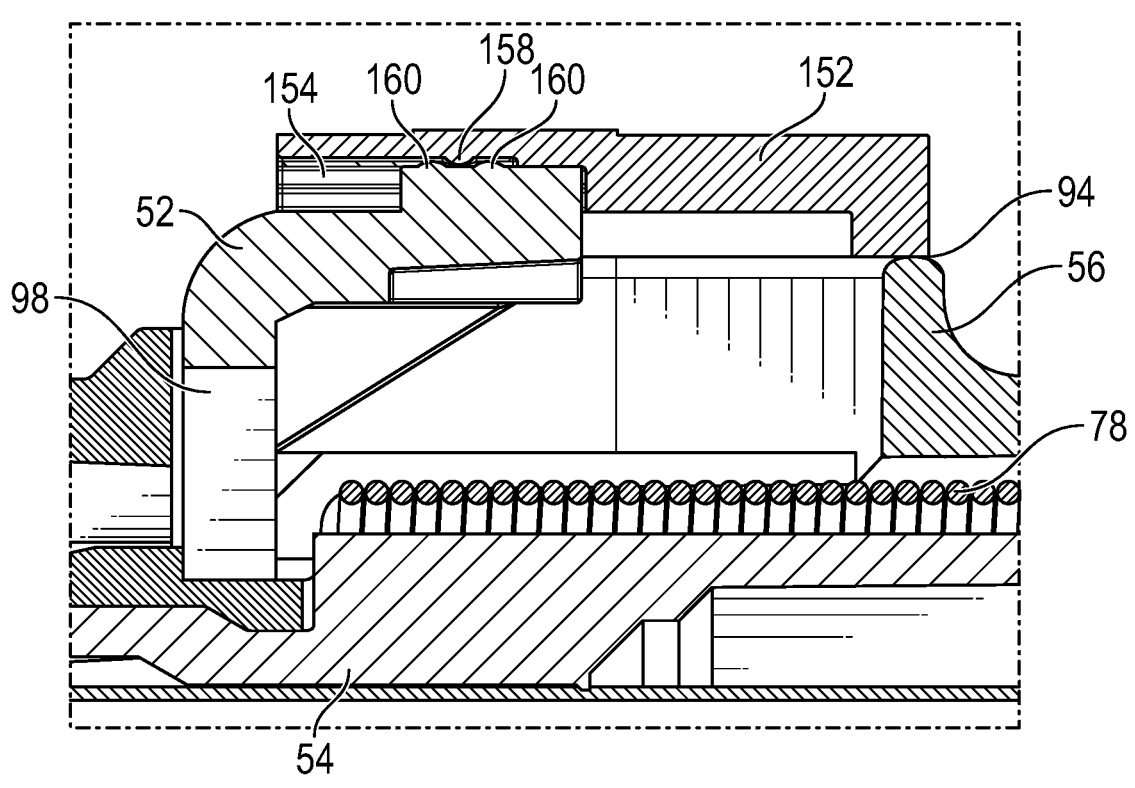
FIG. 11B is a cross-sectional view of a portion of the catheter system of FIG. 10A, according to some embodiments.
Figure 11C:
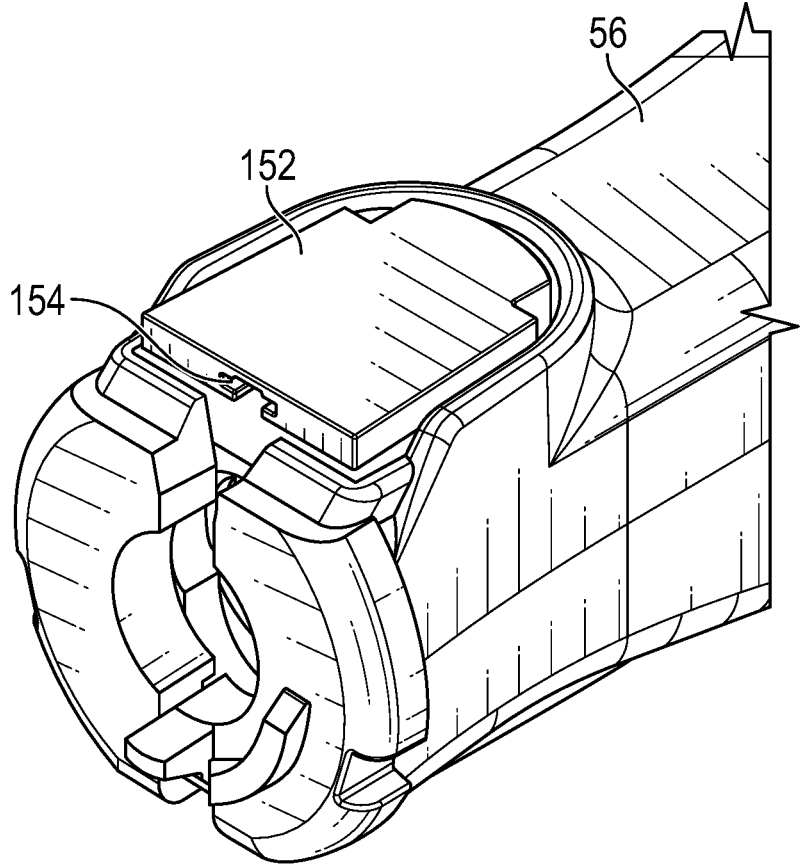
FIG. 11C is a top view of a portion of the catheter system of FIG. 10A, illustrating the slider in an example distal position, with the needle hub removed for illustrative purposes, according to some embodiments.

Referring now to FIGS. 9C-9D, a distal face of the push button 52 contacting the barrel 56, which may include a grip, may include one or more pads 142 to reduce friction between the push button 52 and the barrel 56. The push button 52 of 9C-9D may be similar or identical to the push button 52 of any of the previous Figures in terms of one or more features and/or operation.

Referring now to FIGS. 10A-11C, a catheter system 150 is illustrated, according to some embodiments. The catheter system 150 may be similar or identical to one or more of the prior art catheter system 10 of FIGS. 1-4, the catheter system 50 of FIGS. 5A-5K, the catheter system 110 of FIGS. 7A-7G, and the catheter system 130 of FIGS. 8A-8E in terms of one or more features and/or operation.

The catheter system 150 may include a slider 152, which may include a groove 154. A slider rail 156 of the push button 52 may be disposed within the groove 154 and configured to slide within the groove 154. In a proximal position, the slider 152 may overlap the edge 94 of the barrel 56 to prevent depression of the push button 52. In response to sliding of the slider 152 from the proximal position to a distal position, the slider 152 may be configured to depress when the barrel 56 is spaced apart from the catheter adapter 60. In response to depression of the push button 52, the spring 78 may be configured to expand proximally and move the needle hub 54 proximally within the barrel to retract the introducer needle 74 proximally.

The groove 154 may include a bump 158. The slider rail 156 may include multiple steps 160. When the slider 152 is in the proximal position, the bump 158 may be disposed between the steps 160. In response to sliding of the slider 152 from the proximal position to the distal position, the bump 158 may snap distal to the steps 160.

All examples and conditional language recited herein are intended for pedagogical objects to aid the reader in understanding the invention and the concepts contributed by the inventor to furthering the art and are to be construed as being without limitation to such specifically recited examples and conditions. Although embodiments of the present inventions have been described in detail, it should be understood that the various changes, substitutions, and alterations could be made hereto without departing from the spirit and scope of the invention.

What is claimed:

1. A catheter system, comprising:
    a catheter assembly, comprising:
        a catheter adapter, comprising a distal end, a proximal end, and a catheter adapter lumen extending through the distal end of the catheter adapter and the proximal end of the catheter adapter; and
        a catheter extending from the distal end of the catheter adapter;
    a needle assembly, comprising:
        a barrel;
        an introducer needle comprising a sharp distal tip;
        a needle hub coupled to the introducer needle and movably disposed within the barrel; and
        a spring disposed within the barrel; and a push button disposed in a locked position such that depression of the push button is inhibited, wherein the push button is configured to slide laterally from the locked position to an unlocked position, wherein when the push button is in the unlocked position and the barrel is spaced apart from the catheter adapter, the push button is configured to depress, wherein in response to depression of the push button, the spring is configured to expand proximally and move the needle hub proximally within the barrel to retract the introducer needle proximally.

2. The catheter system of claim 1, wherein an upper surface of the push button comprises a tab generally perpendicular to a longitudinal axis of the catheter system.

3. The catheter system of claim 1, wherein the push button comprises a projection extending in a distal direction, wherein a distal end of the projection comprises an arm, wherein the needle hub comprises a slot, wherein when the push button is in the locked position, the arm is disposed within the slot to inhibit depression of the push button, wherein in response to the push button sliding laterally, the arm is configured to remove from the slot to move the push button from the locked position to the unlocked position.

4. The catheter system of claim 3, wherein the arm extends in an opposite direction as a direction of lateral sliding of the push button from the locked position to the unlocked position.

5. The catheter system of claim 1, wherein an edge of the push button is spaced apart from an edge of the barrel to a create a gap between the push button and the barrel, wherein in response to the push button sliding laterally from the locked position to the unlocked position, the push button closes the gap.

6. The catheter system of claim 1, wherein the push button comprises an opening, wherein the needle hub extends through the opening, wherein the opening comprises an upper arc proximate a lower arc, wherein a center of a circle formed by the upper arc is offset from a center of a circle formed by the lower arc, wherein when the push button is in the locked position, the needle hub is aligned with the center of the circle formed by the lower arc, wherein when the push button is in the unlocked position, the needle hub is aligned with the center of the circle formed by the upper arc.

7. The catheter system of claim 1, wherein a distal face of the push button contacting the barrel comprises a plurality of pads to reduce friction between the push button and the barrel.

8. The catheter system of claim 1, wherein the push button comprises a protrusion contacting an edge of the barrel when the push button is in the locked position, wherein in response to the push button sliding laterally from the locked position to the unlocked position, the protrusion is moved internal to the edge of the barrel such that the push button is configured to depress when the barrel is spaced apart from the catheter adapter.

9. The catheter system of claim 1, wherein an upper surface of the push button is sloped upwardly in a direction of lateral sliding of the push button from the locked position to the unlocked position.

*    *    *    *    *